United States Patent [19]
Flaherty et al.

[11] Patent Number: 5,582,698
[45] Date of Patent: Dec. 10, 1996

[54] SENSOR PACKAGE

[75] Inventors: James E. Flaherty, Attleboro; Robert B. Green, Hopkinton; Steven C. Lepke, Danvers; Richard W. Mason, Millis, all of Mass.

[73] Assignee: Ciba Corning Diagnostics Corp., Delaware, Mass.

[21] Appl. No.: 508,273

[22] Filed: Jul. 27, 1995

Related U.S. Application Data

[62] Division of Ser. No. 266,824, Jun. 27, 1994, Pat. No. 5,494,562.

[51] Int. Cl.$^6$ .................................................. G01N 27/26
[52] U.S. Cl. .................. 204/409; 204/415; 204/403; 204/418; 422/82.01; 422/82.02; 422/82.03
[58] Field of Search ........................... 204/403, 409, 204/415, 418, 422; 422/68.1, 82.01, 82.02, 82.03

[56] References Cited

U.S. PATENT DOCUMENTS

| | | | |
|---|---|---|---|
| 2,891,920 | 6/1959 | Hyde et al. | 260/29.2 |
| 4,044,193 | 8/1977 | Petrow et al. | 429/40 |
| 4,166,143 | 8/1979 | Petrow et al. | 427/115 |
| 4,221,688 | 9/1980 | Johnson et al. | 260/29.2 |
| 4,244,849 | 1/1981 | Saam | 260/29.2 M |
| 4,415,666 | 11/1983 | D'Orazio et al. | 435/179 |
| 4,427,811 | 1/1984 | Elias | 524/96 |
| 4,534,356 | 8/1985 | Papadakis | 204/415 |
| 4,536,274 | 8/1985 | Papadakis et al. | 204/433 |
| 4,571,292 | 2/1986 | Liu et al. | 204/412 |
| 4,679,562 | 7/1987 | Luksha | 128/635 |
| 4,689,309 | 8/1987 | Jones | 436/95 |
| 4,713,165 | 12/1987 | Conover et al. | 204/403 |
| 4,911,794 | 3/1990 | Parce et al. | 204/409 |
| 4,970,145 | 11/1990 | Bennetto et al. | 204/403 |
| 5,160,418 | 11/1992 | Mullen | 204/153 |
| 5,284,568 | 2/1994 | Pace et al. | 204/403 |
| 5,322,063 | 6/1994 | Allen et al. | 204/403 |
| 5,401,376 | 3/1995 | Foos et al. | 204/403 |

FOREIGN PATENT DOCUMENTS

| | | |
|---|---|---|
| 1249333 | 1/1989 | Canada . |
| 207370B1 | 7/1987 | European Pat. Off. . |
| 0470290 | 10/1990 | European Pat. Off. . |
| 53-144883 | 2/1979 | Japan . |

OTHER PUBLICATIONS

Xie, Luo Sheng, *Sensors and Actuators B*, 17(2) (1994) 133–142. no month available.

S. Gernet, *Sensors and Actuators B*, 18(1) (1989) 59–70. no month available.

*Primary Examiner*—Bruce F. Bell
*Attorney, Agent, or Firm*—Judith A. Roesler; Arthur S. Morgenstern

[57] ABSTRACT

A solid state, multi-use electrochemical sensor having an electrically nonconductive substrate, a working electrode, and a semi-permeable membrane covering the working electrode. The working electrode includes an electrically conductive material adhered to a portion of the substrate. A first portion of the conductive material is covered with an electrically insulating dielectric coating, and a second portion of the conductive material is covered with an active layer. The active layer includes a catalytically active quantity of an enzyme carried by platinized carbon powder particles, which are distributed throughout the active layer. A sensor package for incorporating a sensor is provided.

20 Claims, 18 Drawing Sheets

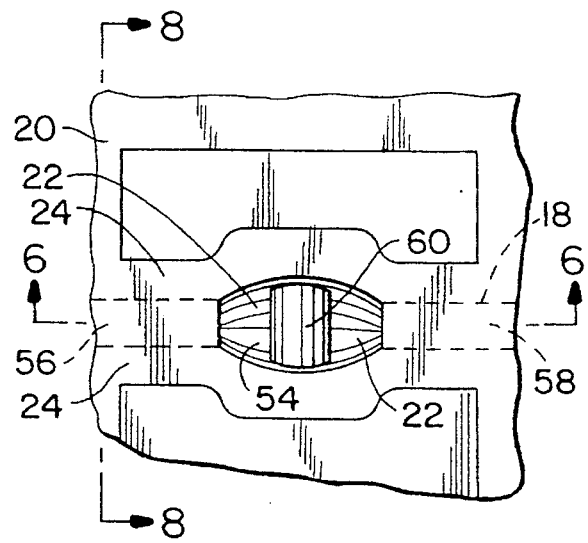
FIG. 5
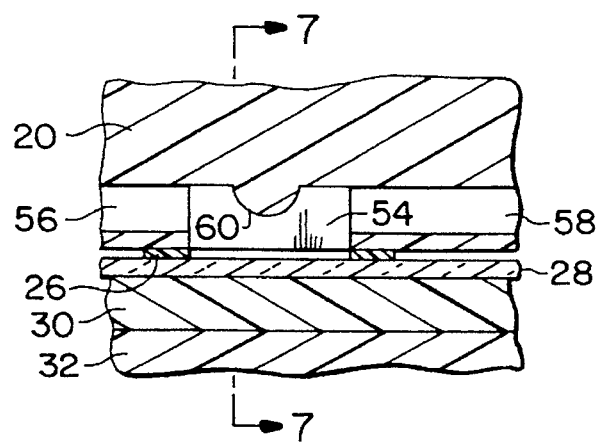
FIG. 6
FIG. 7
FIG. 8
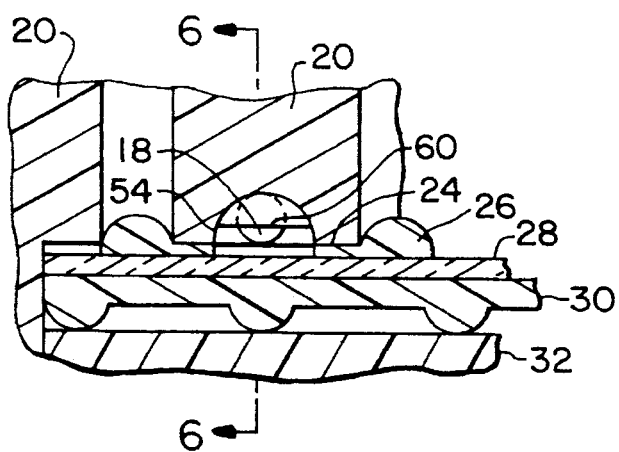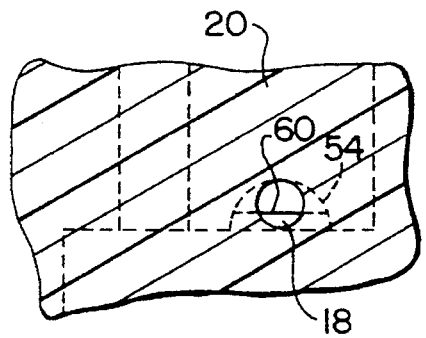

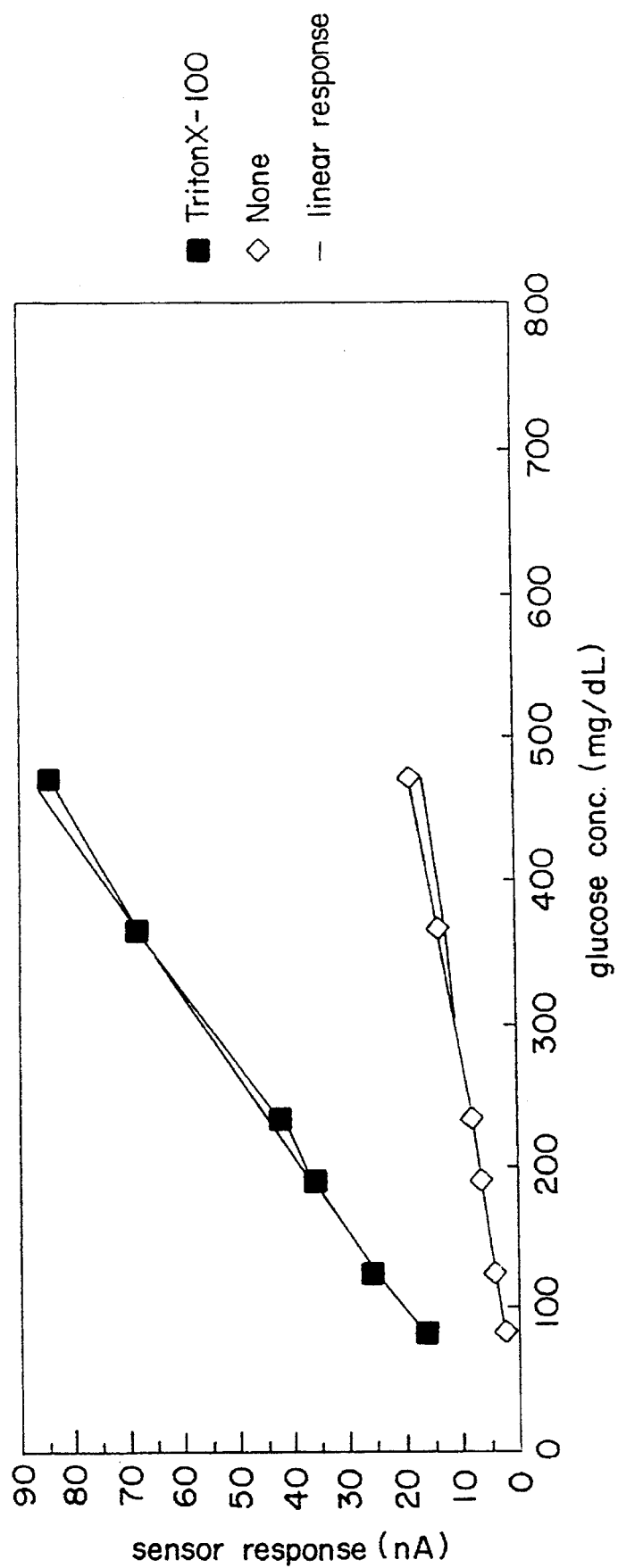

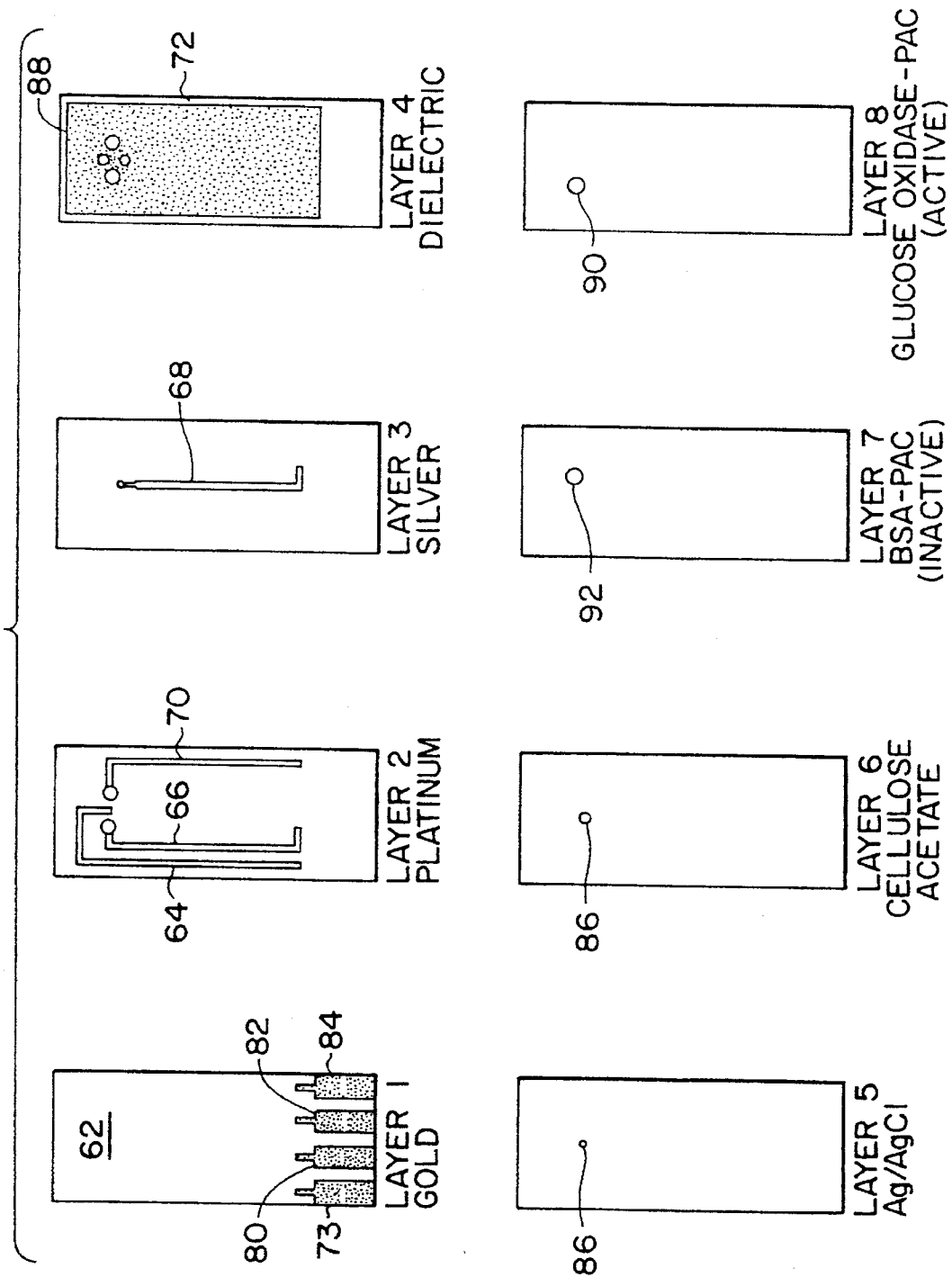

SENSOR PACKAGE

This is a divisional of application Ser. No. 08/266,824 filed on Jun. 27, 1994, now U.S. Pat. No. 5,494,562.

The present invention relates generally to electrochemical sensors and, more particularly, to enzyme catalyzed electrochemical sensors including glucose and lactate sensors. Novel packages incorporating enzyme electrodes having an enzyme contained in an electrically conductive substrate, responding to the catalytic activity of the enzyme in the presence of the substrate are described.

TECHNICAL REVIEW

The concentration of glucose and lactate in the blood is extremely important for maintaining homeostasis. For example, a concentration of glucose below the normal range, or hypoglycemia, can cause unconsciousness and lowered blood pressure, and may even result in death. A concentration of glucose at levels higher than normal, or hyperglycemia, can result in synthesis of fatty acids and cholesterol, and in diabetics, coma. The measurement of the concentration of glucose in a person's blood, therefore, has become a necessity for diabetics who control the level of blood glucose by insulin therapy.

In a clinical setting, accurate and relatively fast determinations of glucose and/or lactate levels can be determined from blood samples utilizing electrochemical sensors. Conventional sensors are fabricated to be large, comprising many serviceable parts, or small, planar-type sensors which may be more convenient in many circumstances. The term "planar" as used herein refers to the well-known procedure of fabricating a substantially planar structure comprising layers of relatively thin materials, for example, using the well-known thick or thin-film techniques. See, for example, Liu et al., U.S. Pat. No. 4,571,292, and Papadakis et al., U.S. Pat. No. 4,536,274, both of which are incorporated herein by reference.

In the clinical setting, it is a goal to maximize the data obtainable from relatively small test sample volumes (microliters) during chemical blood analysis. Fabrication of a sensor sample chamber for holding a blood sample in contact with a sensor is desirable in this regard so that many determinations may be simultaneously performed on a test sample, for example, using a series of interconnected sensors, each constructed to detect a different analyte, from a small test sample volume. However, as a sample chamber is made smaller, the concentration of contaminants in a sample, as those released from sensor components themselves, especially components defining the sample chamber, and/or certain reaction products of the sensor itself is increased. Such contamination may result in premature sensor failure.

There are two major types of glucose or lactate electrode sensors. The first is an electrocatalytic device which utilizes direct oxidation of glucose or lactate for obtaining a measurable response. The second is an enzyme electrode which utilizes an enzyme to convert glucose or lactate to an electroactive product which is then analyzed electrochemically.

With respect to glucose sensors, the latter type of electrode sensors, including an enzyme electrode, converts glucose in the presence of enzymes, such as glucose oxidase, and results in the formation of reaction products including hydrogen peroxide according to the following reactions:

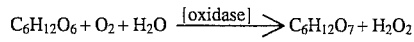

In these reactions, glucose reacts with oxygen to form gluconolactone and hydrogen peroxide. A suitable electrode can then measure the formation of hydrogen peroxide, as an electrical signal. The signal is produced following the transfer of electrons from the peroxide to the electrode, and under suitable conditions the enzyme catalyzed flow of current is proportional to the glucose concentration. Lactate electrode sensors including an enzyme electrode, similarly convert lactate in the presence of enzymes, such as lactate oxidase.

Numerous devices for determination of glucose and lactate have been described, however most of them have some limitation with respect to reproducibility, speed of response, test same volume, number of effective uses, and the range of detection. Some existing commercial methods rely on utilization of hydrogen peroxide measurement as outlined above.

With respect to glucose sensors, in known enzyme electrodes, glucose and oxygen from blood, as well as some interferants, such as ascorbic acid and uric acid diffuse through a primary membrane of the sensor. As the glucose, oxygen and interferants reach a second membrane, an enzyme, such as glucose oxidase, catalyzes the conversion of glucose to hydrogen peroxide and gluconolactone. The hydrogen peroxide may diffuse back through the primary membrane, or it may further diffuse through the secondary membrane to an electrode where it can be reacted to form oxygen and a proton to produce a current proportional to the glucose concentration. The electrode's membrane assembly serves several functions, including selectively allowing the passage of glucose therethrough, providing a location between the primary and secondary membranes for an enzyme to catalyze the reaction between the glucose and oxygen passing through the primary membrane, and allowing only hydrogen peroxide through the secondary membrane to the electrode.

A single-layered electrode membrane was described by Jones in EP Patent No. 207 370 B1. This reference is directed to an electrochemical sensor including three primary components: a metal electrode, a reactive layer of immobilized enzyme directly on an anode, and a single-layered membrane. The membrane disclosed in EP 207,370 B1, is glucose permeable and whole blood compatible, thereby eliminating the need for the secondary membrane typical in prior art sensors. The membrane is formed from a dispersion of a polymerizable silicon-containing compound applied in an incompletely cured form, having a liquid carrier which is essentially insoluble in the dispersed phase and removable from the dispersion during curing. The membrane cures as a continuous layer, film or membrane, having high glucose permeability.

It has been found, however, that the single membrane layer disclosed in EP 207,370 B1 prevents only anionic interfering substances, such as ascorbic acid and uric acid, from passing therethrough. Neutral species, such as acetaminophen, can diffuse through the membrane and influence the sensor's sensitivity and accuracy.

As noted above, enzyme electrodes convert glucose into hydrogen peroxide, which can be reacted to produce a current proportional to the glucose concentration. Enzyme electrodes adapted to measure other analytes have also been described in the art. An enzyme electrode having an electrically conductive support member which consists of, or comprises, a porous layer of resin-bonded carbon or graphite particles is disclosed by Bennetto et al., in U.S. Pat. No. 4,970,145. The carbon or graphite particles have a finely divided platinum group metal intimately mixed therewith, to form a porous, substantially homogeneous, substrate layer into which the enzyme is adsorbed or immobilized. The preferred substrate materials are resin bonded, platinized carbon paper electrodes, comprising platinized carbon powder particles bonded onto a carbon paper substrate using a synthetic resin, preferably polytetrafluoroethylene, as the binder. These electrode materials are manufactured by depositing colloidal size particles of platinum, palladium, or other platinum group metal, onto finely divided particles of carbon or graphite, blending the platinized or palladized carbon or graphite particles with a fluorocarbon resin, preferably polytetrafluoroethylene, and applying the mixture onto an electrically conductive support, such as carbon paper, or a filamentous carbon fiber web.

The above-referenced enzyme electrodes require pre-molding of the graphite or carbon base often under conditions requiring sintering of the molded compact to fuse the binder, which, as noted, is a high melting point hydrophobic synthetic resin. These high temperatures would destroy enzymes, such as glucose oxidase or lactate oxidase.

Enzyme electrodes comprising an enzyme or mixture of enzymes immobilized or adsorbed onto a porous layer of resin bonded platinized or palladized carbon or graphite particles without a high temperature binder have been disclosed by Mullen, in U.S. Pat. No. 5,160,418. Mullen disclosed that the high temperature binders can either be dispensed with entirely or replaced by a low temperature, preferably water soluble or water dispersible binder, such as gelatin (a binder which can be activated at room temperature, which does not require high temperature sintering).

Despite the above improvements in the art, however, a need remains for accurate, multi-use glucose and lactate sensors, incorporating a glucose or lactate and oxygen-permeable membrane and an enzyme electrode. In addition, there is a need for an electrochemical sensor package which can be used with a small blood sample and for extended sampling or uses in a clinical setting. An electrochemical sensor of this type that does not require maintenance, i.e. remembraning, electrode cleaning, etc. would also be desired.

It is therefore an object of the present invention to provide an improved electrochemical sensor, and method of making the same, generally incorporating enzyme electrodes having a metallized carbon base and an overlying silicon-containing protective glucose and/or lactate permeable membrane.

It is a further object of the invention to provide an electrochemical sensor incorporating an interference correcting electrode onto the sensor to provide efficiency over extended sampling periods.

It is a further object of the present invention to provide an improved sensor package, which can be used with a series of interconnected sensors, including a small sample chamber.

It is a still further object of this invention to provide an improvement in a planar electrode comprising using a metallized carbon active layer over a metal contact, and having an outer membrane which enables rapid testing of samples, including blood, to determine glucose and/or lactate concentrations.

It is a still further object of this invention to provide a planar sensor having a small sample chamber which incorporates a velocity compensator to allow fluid flow without incurring problems of insufficient wash-out, i.e. sample carryover, or velocity modification in the chamber, thus enabling fast filling and emptying of the chamber and increasing sample throughput.

It is a still further object of this invention to provide means and method for attaching small resilient electrical leads to a plurality of contacts in an electrical sensor with positive predetermined positioning rapidly and efficiently and with high precision and accuracy.

It is still a further object of the invention to provide a method for post-treating sensors to prolong the storage life or wet-up of the sensor.

It is still a further object of the invention to provide multi-use glucose and lactate sensors having a long life.

It is still a further object of the invention to provide a method of formulating an enzyme into a paste for use in an electrode.

It is still a further object of the invention to provide a method of formulating cellulose acetate into a paste for use in an electrode.

Accordingly, the present invention provides a solid state, planar electrochemical sensor including an electrically non-conductive substrate, a working electrode, and a semi-permeable membrane covering the working electrode, which permits glucose and oxygen or lactate and oxygen to pass through to the electrode. The working electrode includes an electrically conductive material adhered to a portion of the substrate. A first portion of the conductive material is covered with an electrically insulating dielectric coating, and a second portion of the conductive material is covered with an active layer. The active layer includes a catalytically active quantity of an enzyme, such as glucose oxidase or lactate oxidase, carried by platinized carbon powder particles, which are distributed throughout the active layer.

The sensor may further include a counter electrode having a second electrically conductive material adhered to a second portion of the nonconductive substrate. A portion of the second conductive material is covered with the electrically insulating dielectric coating, and at least one portion of the second conductive material remains uncovered.

In one embodiment of the present invention, the nonconductive substrate is made from alumina admixed with a glass binder, and the conductive materials are thick-film pastes of either silver, gold, or platinum. The dielectric coating is made from either ceramics, glasses, polymers, or combinations thereof. The semi-permeable membrane can be formed from cellulose acetate, polyurethane, silicone compounds, and other materials known in the art such as Nafion® material available from E. I. DuPont de Nemours & Co., Wilmington, Del. The preferred membrane is a dispersion of a polymerizable silicon-containing compound applied in an incompletely cured form of a silicone compound dispersed phase in a liquid carrier. The semi-permeable membrane includes a silicone compound having at least about 10.0 percent colloidal silica, by weight. The preferred membrane includes at least about 14.0 percent colloidal silica, by weight.

In another embodiment of the present invention, the electrochemical sensor may further include a reference electrode including a third electrically conductive silver material adhered to a third portion of the substrate. A first portion of the third conductive material is covered with the electrically insulating dielectric coating, and a second portion of the third conductive material remains uncovered by the electrically insulating dielectric coating. The third electrically conductive material typically includes a silver/silver chloride thick-film paste. The second portion of the conductive material is covered by cellulose acetate.

In still another embodiment of the present invention, the electrochemical sensor may further include an interference correcting electrode including a fourth electrically conductive material adhered to a fourth portion of the substrate. A first portion of the conductive material is covered with the electrically insulating dielectric coating, and a second portion of the conductive material is covered with an inactive layer. The inactive layer includes an inactive protein immobilized onto platinized carbon powder particles, which are distributed substantially uniformly throughout the inactive layer.

In another embodiment of the present invention, the semi-permeable membrane is post-treated with a high boiling point, water soluable, hydrophilic liquid anti-drying agent.

In a further aspect of the present invention, an electrochemical sensor package is provided. The package includes a housing having a recess with a perimeter and at least one passageway connected to the recess. A gasket contacts the recess perimeter and a solid state, planar electrochemical sensor, as described above, and forms a seal therebetween. The housing and electrochemical sensor define a sample chamber.

In yet another embodiment of the sensor package of the present invention, the package further includes a contact lead frame. The lead frame includes leads secured to the frame at a first end, and a recess for the sensor at the opposite end. The contact lead frame may further include a stabilizer bar for aligning the leads with contact pads on the surface of the sensor. A groove may also be provided in the package for receipt of the stabilizer bar as the leads are wrapped over the top portion of the lead frame to be aligned with the sensor contact pads. A pad, or the like, may also be provided in the package of the present invention for supporting the sensor in the recess of the contact lead frame.

In another embodiment of the present invention, the sensor package includes a velocity compensator or bump within the sample chamber. The velocity compensator can be a molded part of the housing and preferably faces the sensor.

The method of forming a solid state, planar electrochemical sensor includes selecting a suitable substrate material made from electrically nonconductive material, and forming it into a desired shape and size. An electrically conductive material is then deposited onto a portion of the substrate. Next, a portion of the conductive material is covered with an electrically insulating dielectric coating, and a portion of the conductive material is uncovered so as to define an electrode area. A working electrode is then formed on the electrode area which includes an active layer comprising a catalytically active quantity of an enzyme, such as glucose oxidase or lactate oxidase, immobilized onto platinized carbon powder particles, which are distributed substantially uniformly throughout the active layer. Lastly, a semi-permeable membrane covers the working electrode, which permits glucose and oxygen or lactate and oxygen to pass through to the electrode.

A preferred solid state, planar electrochemical sensor of the present invention is formed by selecting a suitably sized and shaped substrate made of an electrically nonconductive material, such as a ceramic material comprising alumina and a glass binder. Four conductive strips are deposited on top of the substrate so as to extend from a first end to a second end thereof. At the first end, the conductive strips define contact pads for electrical connection, and at the opposite end of the substrate the strips define an electrode area for test sample exposure. The conductive strips may be deposited using thin or thick-film silk-screening techniques using conductive metal pastes of either silver, gold, and/or platinum. An electrically insulating dielectric coating is similarly deposited on top of portions of the conductive strips, while leaving portions of the strips uncovered to define the reference electrode, counter electrode, working electrode, interference correcting electrode, and contact pads. The reference electrode is formed by depositing a layer of silver/silver chloride onto the exposed electrode region. A cellulose acetate layer is then applied over the silver/silver chloride reference electrode to protect the silver chloride from contaminants that would shift the reference potential.

A working electrode is formed by depositing an active layer, comprising a catalytically active quantity of an enzyme immobilized onto to platinized carbon powder particles, upon a conductive strip using similar screen printing techniques. An interference correcting electrode is formed in a manner similar to the working electrode. The interference correcting electrode, however, includes an inactive layer, comprising an inactive protein in place of the catalytically active quantity of an enzyme immobilized onto platinized carbon particles. The interference correcting electrode serves to adjust for electrochemically active neutral species which may diffuse through a semi-permeable cover membrane, which is preferably spun-cast over the electrodes.

In an improvement provided by the present invention, a planar electrode for use in glucose and/or lactate determinations, in vitro, has an insulating base layer, a conductive layer, an overlying active layer and an outer protective membrane permeable to glucose and/or lactate. The improvement of the invention includes the active layer having an enzyme reactive with one of glucose or lactate, and a platinized carbon powder particle portion, so that the active layer is capable of causing formation of hydrogen peroxide in amounts proportional to the amount of the glucose or lactate being tested when they are exposed to the active layer, and the outer protective membrane which is a silicone compound having an additive incorporated therein for enabling transport of glucose or lactate therethrough to enable rapid and accurate determinations of glucose or lactate.

In another improvement of this invention, a multi-use electrochemical sensor is provided having a long life of effective use without maintenance.

In another improvement of this invention, in a planar sensor having a plurality of electrodes positioned in a sample chamber with the sample chamber having a flow-through path, an inlet and an outlet, each having a cross-sectional area less than the cross-sectional area of a portion of the chamber, a velocity compensator is provided. The velocity compensator is a structural barrier mounted in the flow path between the inlet and outlet to reduce the cross-sectional area of the chamber in the flow path so as to prevent contaminants from collecting, and to substantially maintain stability in fluid velocity when flowing through the chamber. The velocity compensator is preferably integral with the sample chamber and extends towards the electrodes without obstructing fluid flow over the electrodes.

In still another improvement in an electrochemical sensor mounted in a housing and having a plurality of electrical contacts spaced close to each other and a plurality of elongated axially extending electrical leads connected to the contacts, the leads are spaced apart by a stabilizer bar. The stabilizer bar is attached to the leads and positively positions the leads to establish electrical contact. The leads are resilient and urged into contact by the stabilizer bar which is preferably mounted on a lead frame base.

Other features of the present invention will become apparent from the followed detailed description when taken in connection with the accompanying drawings. It is to be understood that the drawings are designed for the purposes of illustration only and are not intended as a definition of the limits of the invention.

BRIEF DESCRIPTION OF THE DRAWINGS

The above and other features, objects and advantages of the present invention will be better understood from the following specification when read in conjunction with the accompanying drawings, in which:

FIG. 5 is a magnified partial view of a sample chamber of the sensor package shown in FIG. 2;

FIG. 6 is a cross-sectional side view of the sample chamber shown in FIG. 5, taken along section line 6—6;

FIG. 7 is a cross-sectional side view of the sample chamber shown in FIG. 6, taken along section line 7—7;

FIG. 8 is a cross-sectional side view of the sample chamber shown in FIG. 5, taken along section line 8—8;

FIG. 25 is a view of the steps of formation of a glucose sensor.

DETAILED DESCRIPTION OF THE INVENTION

Figure 1:
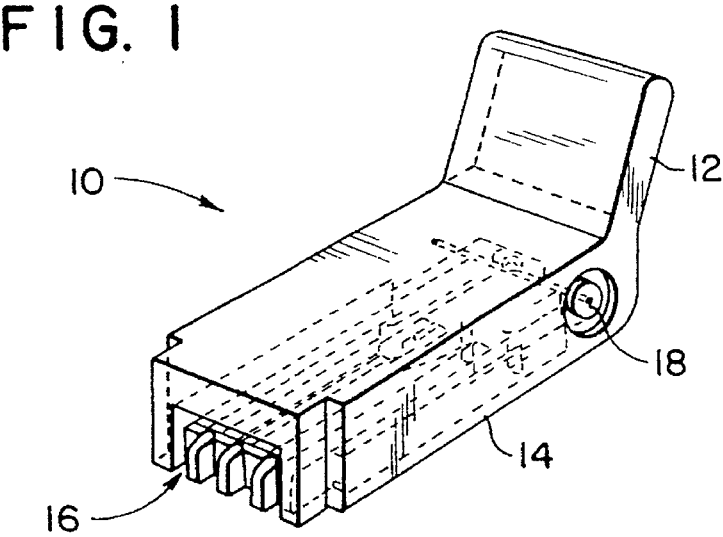
FIG. 1 is a perspective view of an electrochemical sensor package of the present invention.

Referring now to the drawings, in which like reference numerals designate like or corresponding parts throughout the several views, an assembled electrochemical sensor package 10 in accordance with a preferred embodiment of the present invention is illustrated in FIG. 1. Package 10 has a generally J-shaped body, including a handle portion 12, a main body 14, contact portion 16, and fluid or liquid passageway 18.

Figure 2:
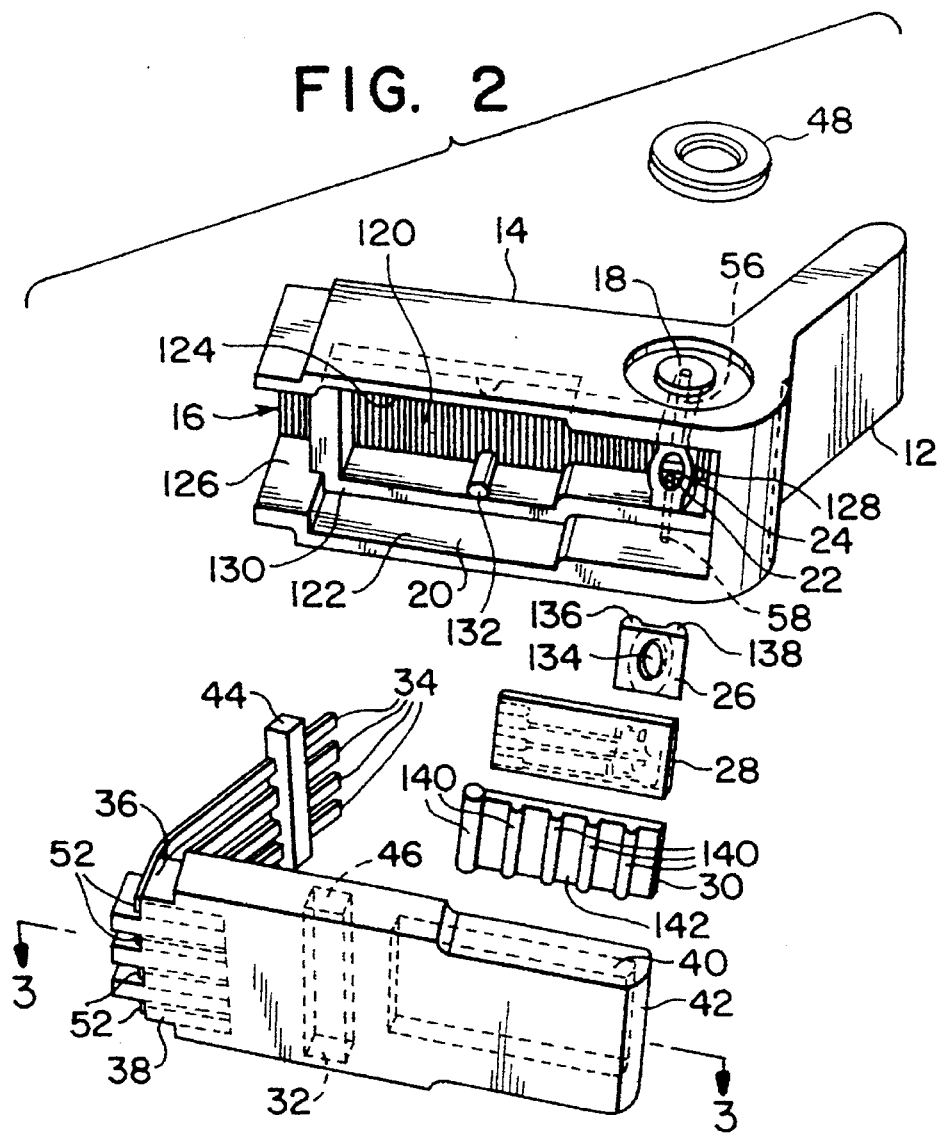
FIG. 2 is an exploded view of the components of the sensor package shown in FIG. 1.

The internal components of sensor package 10 are shown in an exploded view in FIG. 2. Package 10 includes a J-shaped housing 20 having a recess 22 formed therein. The recess 22 which forms a part of a sample chamber 54 (FIG. 5) includes an outer perimeter 24 and at least one passageway 18. Housing 20 has a substantially flat upper portion 120, sidewalls 122, 124, a frontal opening 126, and a rear wall 128 which is contiguous with sensor package handle portion 12. Housing 20 further includes a depressed inner rim 130 and projections 132 which contact the lead frame 32 when package 10 is assembled. A gasket 26 is provided to contact, and form a seal between, the housing perimeter 24 and a sensor 28. Gasket 26 is substantially rectangular-shaped and includes a substantially oval-shaped opening 134, and two raised surfaces 136, 138 which run along the length of gasket opening 134. Gasket raised portions 136, 138 allow gasket 26 to fit around the housing recess perimeter 24, while also allowing recess 22 to be exposed to sensor 28. A sensor pad 30 is provided to support sensor 28. Sensor pad 30 includes a series of transverse protrusions 140 on rear side 142 which provide sensor 28 with added support when package 10 is assembled. Lastly, a contact lead frame 32 is provided to electrically connect sensor 28 to an instrument (not shown) which can measure and convert a current to determine analyte concentration, i.e. glucose or lactate. Contact lead frame 32 includes four leads 34 secured to a base 36 at a first end portion 38, and a sensor recess 40 at a second end portion 42. The lead frame 32 can also include a stabilizer bar 44 for holding the leads in a predetermined position with respect to each other and aligning the leads 34 with the sensor 28. An additional recess 46 can be included for receipt of stabilizer bar 44. It is also noted that an electrode O-ring 48, commercially available from Ciba Corning Diagnostics Corp. or the like, can be provided to maintain a seal between adjacent sensor packages, or a fluid conduit (not shown), each different sensor used to simultaneously detect different analytes from the same fluid sample.

Figure 3:
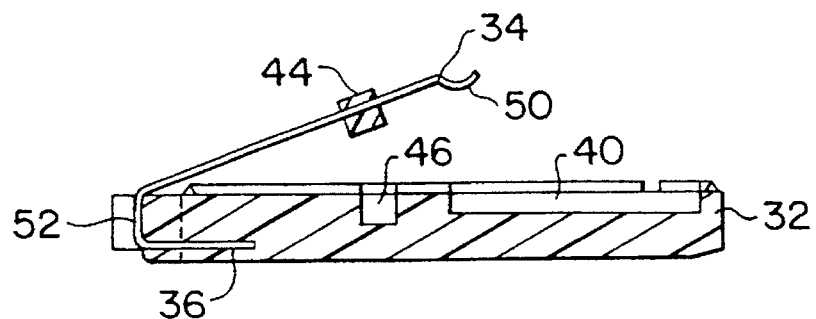
FIG. 3 is a cross-sectional side view of a contact lead frame shown in FIG. 2, with its leads partially open, taken along section line 3—3.
Figure 4:
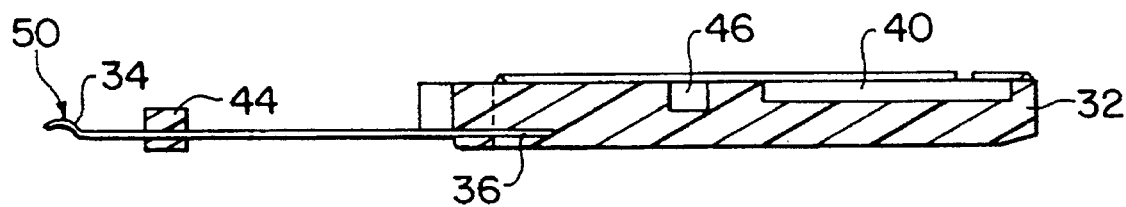
FIG. 4 is a cross-sectional side view of the contact lead frame shown in FIG. 3, with its leads wide open.

Referring now to FIGS. 3 and 4, a cross-sectional side view of contact lead frame 32 taken along section line 3—3, is shown with its leads partially and wide open. As noted above, to provide an interface system between an instrument and contacts on the sensor 28 (described below), contact lead frame 32, including plural leads 34 secured to base 36 at end portion 38, is provided. Leads 34 are typically made from a highly conductive, malleable metal, such as copper. Preferably, leads 34 are made of a highly conductive, malleable material, which is beryllium, silver, gold, or platinum plated, due to the lower cost of plated material. Most preferably, photo-etched, gold plated leads 34 are used due to their high conductivity. The leads 34 are molded into one end 38 of the contact lead frame 32. Lead frame 32 can be formed of any material that is compatible with, and can be secured to, the sensor package housing 20. Typically, lead frame 32 is made from a rigid, durable material such as glass, ceramic, stainless steel, or a plastic material such as acrylic, polyester, polycarbonate, polyvinyl chloride, and the like. Preferably, an acrylic plastic material, such as V825 acrylic, available from Rohm & Haas Corp., Philadelphia, Pa., is used to mold lead frame 32 due to its strength, durability, relatively low cost and ease of processing.

During assembly of the sensor package 10, sensor 28 is placed into recess 40 and leads 34 are bent around the lead frame 32 until they make contact with the sensor. Leads 34 contact the sensor with rounded spring tips 50 which apply constant pressure on the sensor contacts. Stabilizer bar 44, which aligns the leads 34 with the sensor contacts, is secured in recess 46 after the leads are bent around the frame.

Preferably, the stabilizer bar, if present, is solvent cemented in place in recess 46. Instrument contact surfaces 52, which are exposed after the sensor package 10 is assembled, are formed as the leads are bent over the frame (as shown in FIG. 3). Once the leads are in contact with the sensor, housing 20 is placed over the lead frame 32. The housing and lead frame are then secured together by being snap-fit, ultrasonically welded, adhesive bonded, or by other methods known to those skilled in the art.

Referring now to FIGS. 5–8, a magnified view of a sample chamber 54 of the sensor package 10 is shown. As noted above, sample chamber 54 is defined by the housing 20, the outer perimeter 24 around recess 22, gasket 26, and the sensor 28. At least one passageway 18, having an inlet 56 and an outlet 58, is provided to allow passage of a fluid sample, such as blood, into and out of sample chamber 54. Although, in the embodiment illustrated, inlet 56 and outlet 58 pass through housing 20, these openings can be formed in any manner to provide a passageway through which a fluid sample could reach sample chamber 54. For example, openings, or channels, could be formed in the gasket 26, or other part(s) of the sensor package 10.

Figure 5A:
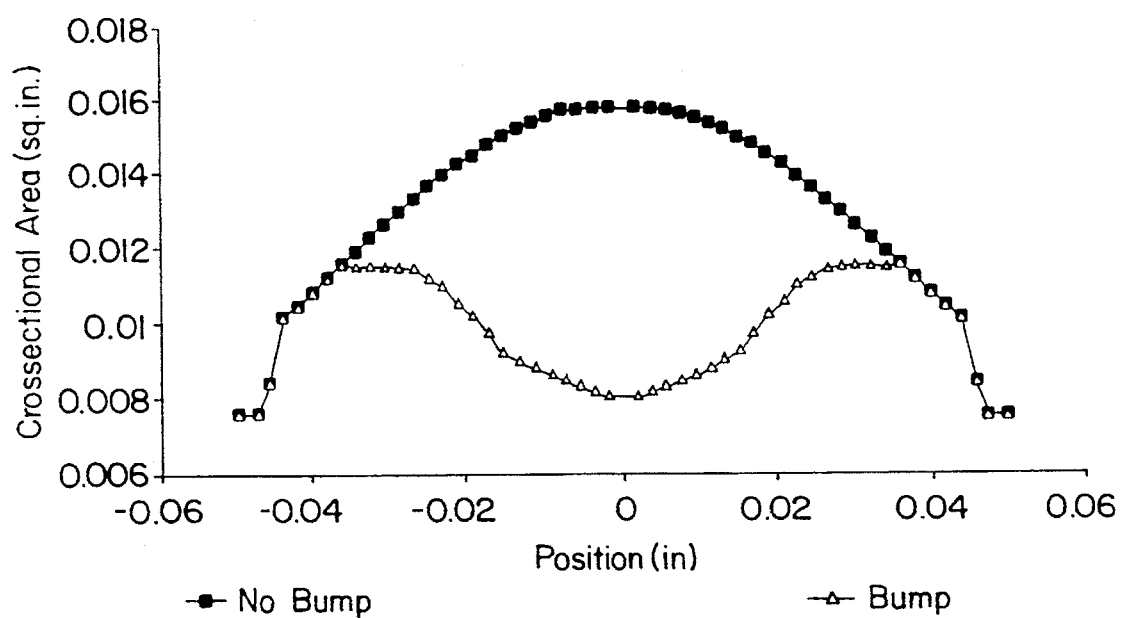
FIG. 5A is a graphical illustration of the cross-sectional area of the sample chamber shown in FIG. 5 versus the position along the chamber flow path, with and without a velocity compensator (bump)
Figure 5B:
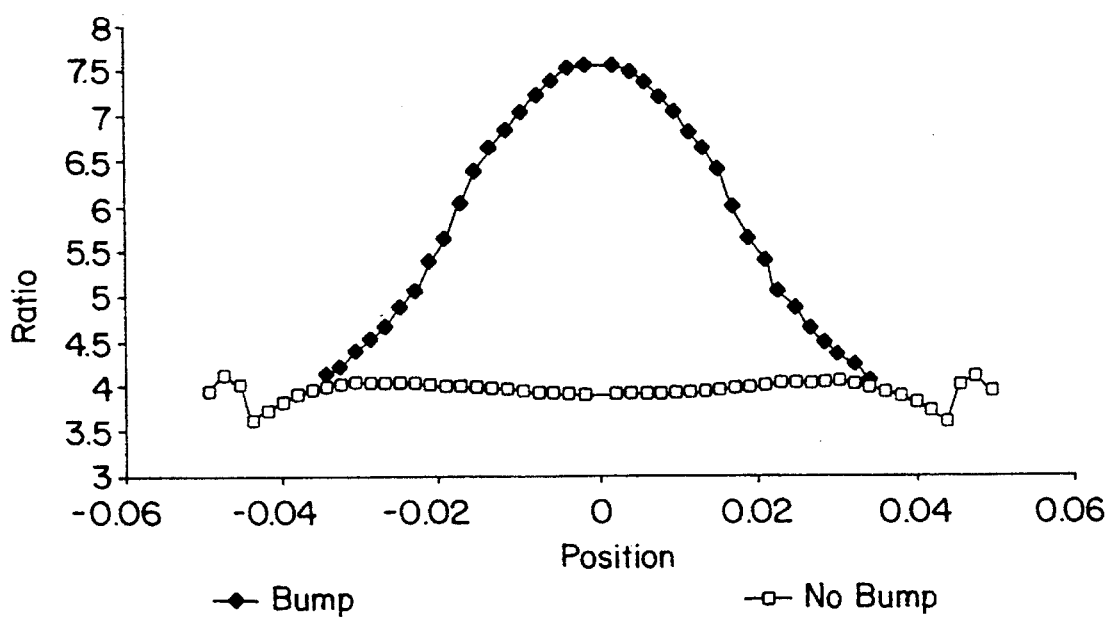
FIG. 5B is a graphical illustration of the ratio of sensing area to flow path cross-sectional area of the sample chamber shown in FIG. 5 versus the position along the chamber flow path, with and without the velocity compensator.
Figure 6A:
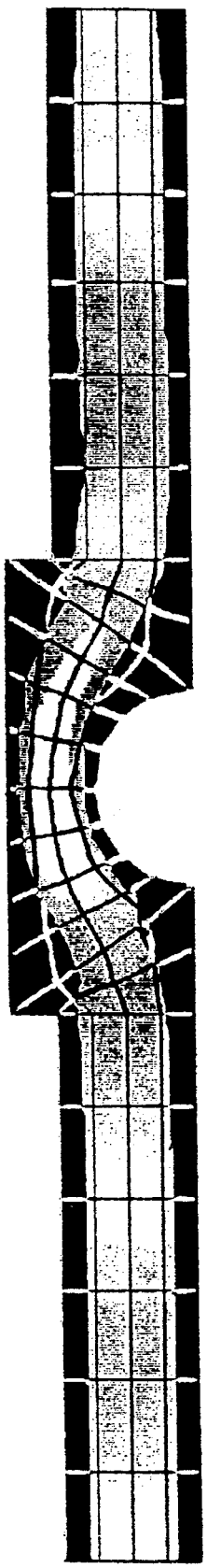
FIG. 6A is a cross-sectional side view of the sample chamber shown in FIG. 5 taken along section line 6—6, showing the velocity of fluid flow with the velocity compensator (velocity: white>black)

The sample chamber 54 of the present sensor package 10 also includes a velocity compensator 60 (Bump), which reduces the internal volume of the chamber and creates a cross-sectional area close to that of the inlet 56 and outlet 58. FIG. 5A graphically illustrates the sample chamber 54 cross-sectional area along the chamber flow path, with and without velocity compensator 60. As shown in the graph, the cross-sectional area of the sample chamber at the velocity compensator approaches that of the inlet and outlet. The velocity compensator or bump acts as a structural director of fluid flow. Conventional sample delivery systems experience problems such as carryover of previous sample materials, and trapped air bubbles which are present or within the leading edge of the sample fluid to address a problem common to conventional sample delivery system. Typically, as a sample enters the chamber 54 its flow velocity abruptly slows until the chamber is full. The sample velocity then increases to its initial level, leaving the solution at the chamber walls stagnant. Although sample chambers are washed between measurements, air bubbles and fluid can become trapped in the chamber in stagnant areas. These air bubbles and residual fluid effect the accuracy of the sample measurement. The velocity compensator 60 of the present invention, therefore, keeps the flow velocity stable within the chamber, and reduces or eliminates the stagnant areas where bubbles and fluid can collect. Referring to FIGS. 6A and 6B, the velocity of fluid flow through the sample chamber is substantially uniform in the presence of the velocity compensator. In addition, velocity compensator 60 allows the use of a large sensing area with relatively small inlet 56 and outlet 58 cross-sections. FIG. 5B graphically illustrates the ratio of sensing area to flow path cross-sectional area along the chamber flow path, with and without velocity compensator 60. Because the cross-sectional area of the chamber 54 is reduced (as shown in FIG. 5A) with the velocity compensator 60 in place, the ratio of sensing area to flow path is increased. This aspect of the present invention allows fluid samples to more efficiently contact sensor 28 as they are passed through package 10. Moreover, by positioning the velocity compensator 60 facing the sensor 28, samples are directed toward the sensor 28 while bubbles are substantially eliminated.

Figure 6A:
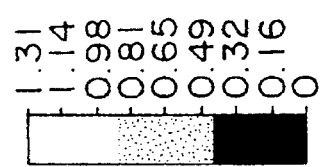
Figure 6B:
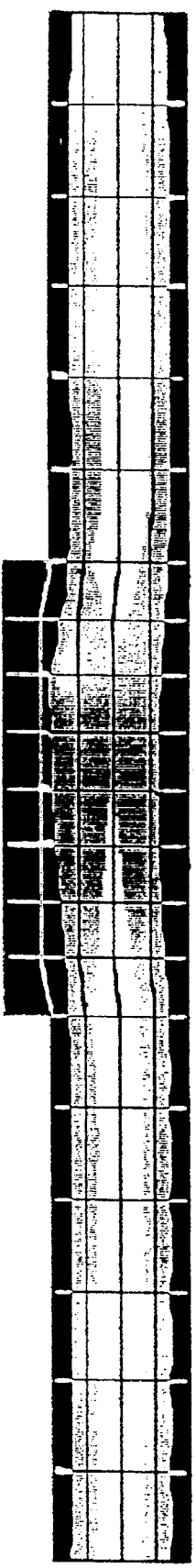
FIG. 6B is a cross-sectional side view of the sample chamber shown in FIG. 5 taken along section line 6—6, showing the velocity of fluid flow without the velocity compensator (velocity: white>black).

FIG. 6 illustrates a cross-sectional side view of the sample chamber 54, taken along section line 6—6. The velocity compensator 60 is shown as a molded part of housing 20. Although shown having a rounded shape, a variety of smooth, sloped shapes, without stagnant areas, can be used. Furthermore, although shown as a molded part of the housing, velocity compensator 60 can be a separate component, added to sample chamber 54.

Inlet 56 and outlet 58 portions are shown leading in and out of chamber 54. These sample paths typically have diameters between about 0.02 inch and about 0.04 inch; preferably, the diameters are about 0.03 inch. The sample chamber 54 has a sample diameter, with the velocity compensator 60, of at least the size of the sample paths to about 0.06 inch. FIG. 8 shows a side view of sensor package 10, taken along section line 8—8, through passageway 18. This view illustrates the relative sizes of the velocity compensator 60, sample chamber 54, and passageway 18.

Housing 20, as well as inlet 56 and outlet 58, and velocity compensator 60, can be fabricated from any material that is unreactive with a sample which passes into sample chamber 54 during analysis. For example, materials such as glass, ceramics, stainless steel, or plastic materials such as acrylic, polyester, polycarbonate, polyvinyl chloride, and the like.

Preferably, a clear, transparent acrylic plastic material, such as V825 acrylic from Rohm & Haas, is used to mold these parts due to its strength, durability, relatively low cost and ease of processing.

Gasket 26, shown in FIGS. 6 and 7, is typically formed from a material which, when held firmly between recess perimeter 24 and sensor 28, forms a seal around sample chamber 54 through which the passage of fluids is substantially prevented.

Typically, gasket 26 is formulated from a durable organic polymer which does not creep or flow when stressed, has a low durometer rating, and can be slightly hygroscopic. Preferably, a material used in the fabrication of gasket 26 has a hardness of between 10 and 100 on the Shore A scale; more preferably, a hardness of from about 40 to about 70 on the Shore A scale; and most preferably, a hardness of from about 45 to about 55 on the Shore A scale.

Because gasket 26 is typically an organic polymer, it is fabricated so as not to contain a substantial amount of any mobile extractable materials, such as plasticizers, which may leach into sensor 28. Additionally, as is the case for other sensor components as described above, it is important the material selected for formation of gasket 26 be free of any species which could migrate into a sample in chamber 54, affecting electrochemical measurements, and/or destroying sensor components. Material used in the formation of gasket 26 is preferably selected to be essentially free of mobile transition and main group metals, especially battery metals such as iron, cobalt, nickel, lead, copper, extractables, and species such as sulfides which are deleterious to preferred electrode materials.

Gasket 26 is typically formed form a highly cross-linked elastomeric compound. Any elastomeric material which meets all the purity and physical requirements listed above may serve. Most preferably, Sarlink™ 2450 elastomeric material from DSM having a hardness of about 50 on the Shore A scale is used to form gasket 26.

Sensor pad 30, also shown in FIGS. 6 and 7, can be formed of a material similar to that used to form gasket 26. Pad 30 is formed of a durable organic polymer which does not creep or flow when stressed, and has a low durometer. Preferably, a material used to form pad 30 has a hardness of between 40 and 60 on the Shore A scale. Most preferably, a silicone rubber or material such as Sarlink 2450 is used to form pad 30.

According to the present invention, a sample chamber 54 of any size can be fabricated. Fabrication of a large sample chamber may be advantageous in some circumstances. As noted above, however, in the field of electrochemical analysis of blood, it is commonly desirable to perform as many analyte analyses as possible on a very small volume of blood. Thus, according to a preferred embodiment of the present invention, it is desirable to fabricate sensor 28 with a sample chamber 54 that is as small as possible. Using the novel materials and methods of the present invention a sensor may effectively be utilized for a period of at least thirty (30) days, or the measurement of at least one thousand (1,000) blood samples having a sample chamber with a volume of less than about 10.0 μl (microliters); and preferably, from about 3.0 to about 5.0 μl.

Figure 9A:
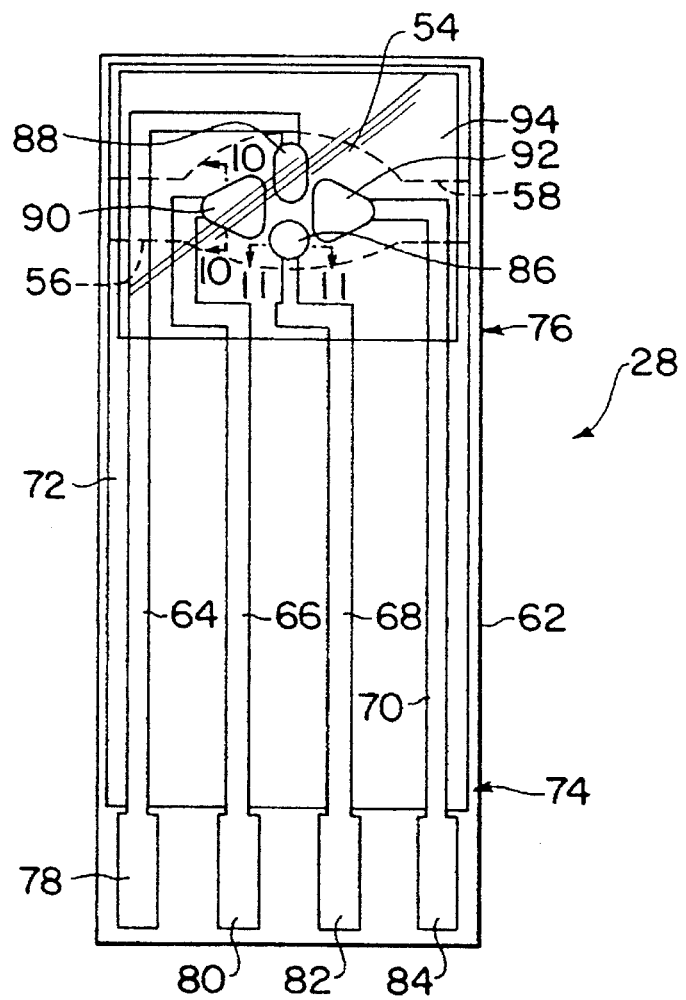
FIG. 9A is a magnified top plan view of a sensor used in the sensor package shown in FIG. 1.

Referring now to FIGS. 9A and 9B through 11, 25, and Table I, a planar electrochemical sensor 28 in accordance with a preferred embodiment of the present invention is shown. FIG. 9A also shows phantom outlines of sample chamber 54, inlet 56 and outlet 58. These features are shown to illustrate the relative position of electrodes 86, 88, 90, and 92 described below to the flow path of a sample to be tested. Sensor 28 includes substantially planar substrate 62, conductive metal strips 64, 66, 68, and 70 deposited thereupon, and dielectric layer 72 deposited on substrate 62 so as to cover portions of conductive strips 64, 66, 68, and 70, while leaving portions of some of the strips uncovered.

Substrate 62 is formed from any substantially electrically insulating material such as ceramic, glass, refractory, polymers or combinations thereof. Formation of such an insulating substrate as a mechanical support or base is common knowledge to those of ordinary skill in the art. In the preferred embodiment, the substrate comprises approximately 96% alumina and approximately 4% glass binder. A suitable material comprising the preferred composition is available from Coors Ceramic Company, Grand Junction, Colo. Although in the preferred embodiments of the present invention a single substrate forms the foundation of sensor 28, a plurality of substrates can also be used, each supporting separate sensor components, and/or helping to support sensor components supported by other substrates.

Conductive strips 64, 66, 68 and 70 are deposited atop substrate 62 so as to extend from a first end 74 to a second end 76 thereof in a preferred embodiment. At first end 74, the conductive strips are typically deposited so as to be wide enough to define contact pads 78, 80, 82, and 84, respectively. At second end 76, the conductive strips are typically deposited so as to be somewhat narrower, exposed regions of which may define electrodes, as described below.

Conductive strips 64, 66, 68 and 70 may be deposited using well known thin or thick-film techniques. Typically, a compound including a metal is applied via typical thick-film screening to substrate 62, and the applied compound and substrate are then fired to sinter the active metal and to co-adhere the active metal to the substrate. The electroactive metal may comprise any conductive metal, for example, silver, platinum or gold, which is not oxidized or reduced in a potential range in which oxidation or reduction of any species to be measured occurs. Additionally, materials selected for fabrication of conductive strips 64, 66, 68 and 70 are desirably selected so as to be free of any impurities such as battery metals (electrochemically active in water) which are typically present in off-the-shelf materials commercially available for wire bonding, soldering, or welding. See EP-A-9481090.2 or U.S. Ser. No. 08/045,847 filed Apr. 9, 1993 which is incorporated herein by reference.

Many thick-film pastes suitable for use in the present invention are commercially available, such as a silver pastes available as product number 3571UF/Ag from Metech, Inc., of Elverson, Pa. (Metech), silver chloride available as product number 2539/Ag/AgCl from Metech; gold pastes available as product number PC10231/Au from Metech, and platinum paste available as product number PC10208/Pt from Metech.

With specific regard to conductive strip 66, which defines in part a working electrode 90 a preferred material is a very high purity platinum thick-film paste. Conductive strip 68 preferably comprises a layer of silver deposited atop substrate 62 with a layer of silver/silver chloride deposited thereupon in the electrode region, discussed below, to create a reference electrode 86. A layer of cellulose acetate is deposited atop the layer of silver chloride. Conductive strips 64, 66 and 70 comprise a platinum thick-film paste in preferred embodiments.

Employment of a silver reference electrode is within the scope of the present invention. Modification of the teachings of the present invention with respect to voltage settings, upon the substitution of a silver reference electrode for a silver/silver chloride reference electrode, would be easily made by one of ordinary skill in the art.

At the second end 76 of substrate 62, dielectric layer 72 is deposited so as to cover portions of conductive strips 64, 66, 68 and 70, while leaving portions of the conductive strips uncovered so as to define reference electrode 86, counter electrode 88, working electrode 90, interference correcting electrode 92, and contact pads 78, 80, 82, and 84. Material selected for fabrication of the dielectric layer 72 is desirably electrically insulating and non-porous, free of impurities which may be subject to oxidation or reduction in the potential range of any species or analyte to be measured, as described above, and is further selected so as to be free of mobile ions that would potentially carry charge and interfere with the activity of any electrolyte employed in the sensor. Further, dielectric 72 is selected so as to firmly adhere to substrate 62 and conductive strips 64, 66, 68, and 70, so as to allow electrodes 86, 88, 90, and 92 to be electrically addressable, while effectively electrically insulating portions covered by the dielectric. Materials such as ceramics, glass, refractory materials, polymeric materials, or combinations thereof are well known as dielectric materials and are suitable for use as a dielectric in the present invention. A preferred material is commercially available as Product Number 9615, a ceramic material from E. I. DuPont de Nemours & Co., Electronics Department, Wilmington, Del.

With respect to materials advantageously selected for fabrication of conductive strips 64, 66, 68, and 70, it is noted that material selection becomes less important in regions of the strips which define contact pads 78, 80, 82 and 84 and which connect the bonding pads to regions which define electrodes. For example, the contact pads and regions of the conductive strips connecting them to the electrodes may be fabricated from any conducting material that adheres to substrate 62 and that does not interfere with the electrical insulation function of dielectric layer 72. According to one embodiment, the contact pads and regions of the conductive strips connecting them to the electrodes are fabricated from a gold paste.

In addition to the material selection parameters discussed above, and as discussed with respect to selection of the dielectric material, it is advantageous in the fabrication of a sensor to select materials for fabrication of the substrate, the conductive strips, and the dielectric layer such that good adherence is achieved between adjacent layers, that is, delamination is minimized. See EP-A-94810190.2 or U.S. Ser. No. 08/045,847 filed Apr. 9, 1993. If good adherence is not achieved, reference, counter, working and interference correcting electrodes 86, 88, 90, and 92, will not be well-defined which in one embodiment is defined by a screen used in the thick-film deposition process, and disadvantageous electrochemistry will result.

Figure 10:
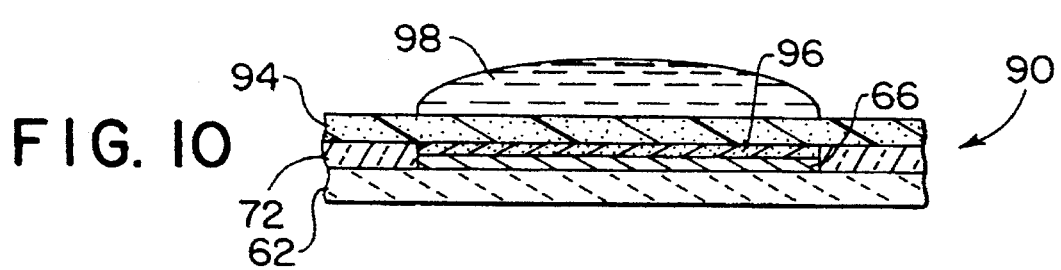
FIG. 10 is a cross-sectional side view of a working electrode used in the sensor shown in FIG. 9A, taken along section line 10—10.

A cross-sectional side view of working electrode 90, taken along section line 10—10, is illustrated in FIG. 10. As described above, conductive strip 66 is deposited upon substrate 62, and dielectric layer 72 covers portions of conductive strip 66 leaving a portion uncovered to define a working electrode area. An active layer 96, comprising a catalytically active quantity of an enzyme immobilized onto platinized carbon powder particles, is deposited upon conductive strip 66 using techniques similar to the deposition of conductive strips 64, 66, 68 and 70. Typically, thick-film screen printing at low temperature is used to apply an active paste to conductive strip 66 in order to limit thermal damage to the enzyme, see Table I.

As noted, active layer 96 comprises an enzyme immobilized into an electrically conducting support member which consists of or comprises a porous layer of resin-bonded carbon or graphite particles. The particles have intimately mixed therewith, or deposited or adsorbed onto the surface of the individual particles prior to bonding to form the layer, a finely divided platinum group metal to form a porous, substrate layer onto which the enzyme is adsorbed or immobilized and comprising a substantially heterogeneous layer of resin-bonded carbon or graphite particles with the platinum group metal adsorbed on the carbon or graphite particles. An enzyme immobilized or adsorbed onto a porous layer of resin bonded platinized carbon particles is disclosed by Mullen, in U.S. Pat. No. 5,160,418 and Bennetto et al., in U.S. Pat. No. 4,970,145, both of which are incorporated by reference. The active layer 96 may alternatively be formed by first depositing the finely divided platinum group metal, optionally preadsorbed onto or admixed with finely divided carbon or graphite, with or without all or some of the resin binder, if used, on the surface of the electrically conductive substrate, or conductive strip 66.

The platinum group metal in finely divided elemental form, including platinum, palladium, iridium, or rhodium, may be replaced by the corresponding oxides, such as platinum or palladium oxide. Therefore, all references herein to a platinized material are to be taken as including a platinum group metal, as described above, and/or corresponding oxides-containing material unless the context requires otherwise.

Any suitable carbon or graphite powder which readily permits the subsequent immobilization of an enzyme may be used to form the active layer. To this end, carbon powder should be used having a high density of functional groups, such as carboxylate, amino and sulfur-containing groups, on the surface, as opposed to the more vitreous and glassy carbons, which bind enzymes only poorly. Typically, carbon or graphite powder particle size ranges from between about 3.0 and about 50.0 nm; preferably, particle sizes range from between about 5.0 and 30.0 nm.

Platinum may be deposited on the carbon particles in any convenient fashion, for example, vapor phase deposition, electrochemical deposition, or simple adsorption from colloidal suspension to give platinum group metal loadings in the range of between about 0.1 to about 20.0 percent, by weight, based on the weight of carbon. Preferably, the platinum group metal loadings are between about 5.0 to about 15.0 percent by weight. These limits are, however, practical rather than critical. Below about 1.0 percent platinum group metal, the output signal falls to a level which, in practical terms, is too low to be measured except by very sensitive apparatus; above about 20.0 percent, the loading of platinum group metal becomes uneconomic, with little additional benefit in terms of increased response or sensitivity. In the preferred technique, the carbon powder is platinized by the oxidative decomposition of a platinum compound such as chloroplatinic acid or, more preferably, a complex of platinum or palladium with an oxidadizable ligand, in the presence of the carbon powder, thereby to deposit colloidal size platinum or palladium direct upon the surface of the carbon particle, in the manner taught, for example, by Petrow et al., in U.S. Pat. Nos. 4,044,193 and 4,166,143, both of which are incorporated herein by reference. Preferably, the platinum group metal or oxide particles have a particle size in the range of between about 1.0 nm to about 20.0 nm, and most preferably are of a colloidal size in the range of between about 1.0 nm to about 4.0 nm.

The preferred active layer substrate used in accordance with the present invention are, in fact, commercially available materials, sold under the name PLATINUM ON CARBON BLACK from E-TEK, Inc., Framingham, Mass. An enzyme, such as glucose oxidase, or lactate oxidase, can be immobilized onto platinized carbon powder particles, prepared by the deposition of colloidal platinum having a particle size of between about 1.5 to about 2.5 nm onto the carbon powder, having a nominal particle size of about 30.0 nm, by the oxidative decomposition of complex platinum sulfite acid (II) using $H_2O_2$.

In the present invention, the platinum activated carbon is treated in a phosphate buffer formulation having a pH of about 7.5. The platinum activated carbon is added to the buffer to neutralize any sulfuric acid present from the formation of the platinized carbon powder particles. To the platinum activated carbon and buffer mixture a co-protein, such as bovine serum albumin, is added to adsorb onto the carbon. The bovine serum albumin is added to help stabilize the enzyme, such as glucose oxidase, as is known to those skilled in the art. A binder, such as a commercially available resin solution sold under product number 8101RS from Metech, is then added to the bovine serum albumin-platinum activated carbon mixture. The binder material, as noted above, acts to hold the components of the active layer together. To this mixture, a surfactant may be added to provide better printing flow characteristics when active layer 96 is screen printed upon conductive strip 66. An additional benefit of the surfactant is to act as a wetting agent for the sensor during use. The active layer 96 being comprised of a hydrophobic binder becomes difficult to wet with water after it is fully dried. The surfactant facilitates this wetup. The surfactant material used can be any liquid surfactant, known to those skilled in the art, which is water soluble and exhibits a hydrophilic lipophilic balance (HLB) in the range of 12–16. Typical surfactant materials for use in this regard can be alkylarylpolyether alcohols, such as alkylphenoxypolyethoxyethanol. One such material is sold under the trademark Triton® from Union Carbide Chemicals and Plastics Co., Inc., Danbury, Conn. The preferred material for use in the present application is Triton® X-100 surfactant (HLB 13.5). After these components are milled, a resin thinner may be added to adjust the active layer 96 viscosity for printing purposes. Typically, a petroleum solvent-based resin thinner is used to bring the paste viscosity within the range of between 10,000 to about 100,000 centipoise. Resin thinners for this purpose are commercially available as product number 8101 thinner from Metech. An enzyme, such as glucose oxidase or lactate oxidase, is then added to the mixture, and the final paste is screen printed upon conductive strip 66. Other enzymes may be similarly added to the mixture to prepare active layers specific for other analytes.

It is preferred to put the active layer down last, i.e. before depositing the cover membrane, to minimize the thermal impact to the enzyme from other steps in the sensor formation, see Table I and FIG. 25.

Interference correcting electrode 92 is formed in a manner similar to the working electrode 90. The interference correcting electrode 92, however, includes an inactive layer (not shown) which is made using the same components and method used in a process of forming the working electrode, however, an inactive or nonreactive protein, such as the bovine serum albumin is added to the mixture of bovine serum albumin-platinum activated carbon, resin, surfactant, and thinner. As noted above, the interference correcting electrode serves to adjust for any interfering species, such as the neutral species acetaminophen, diffusing through a semipermeable membrane layer 94 (discussed below) on top of electrodes 86, 88, 90, and 92.

Figure 11:
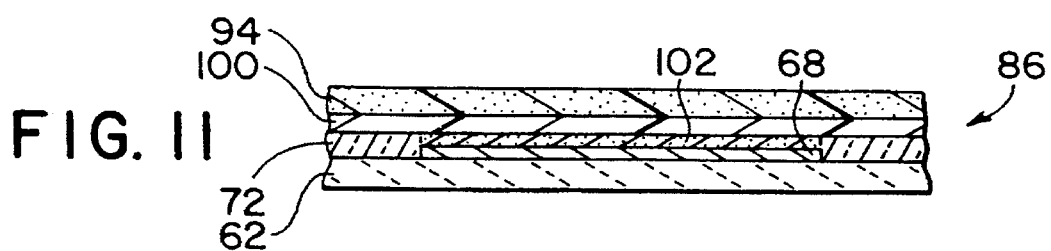
FIG. 11 is a cross-sectional side view of a reference electrode used in the sensor shown in FIG. 9A, taken along section line 11—11.

Referring now to FIG. 11, a cross-sectional side view of reference electrode 86, taken along section line 11—11, is shown. Reference electrode 86, as noted above, is formed as a conductive strip 68, preferably comprising a layer of silver is deposited thereon. Dielectric layer 72 is deposited covering a portion of conductive strip 68, while leaving a portion uncovered to define the electrode areas and contact pads. A silver/silver chloride layer 102 is deposited upon conductive strip 68 by screen printing techniques known to those of skill in the art. Silver/silver chloride reference electrode inks, such as those available as product number 2359 from Metech, are developed to provide a standard reference electrode utilizing the silver/silver chloride couple.

Reference electrode stability measurements showed that over a period of several days, the potential of the reference electrode (86) shifted upon exposure of the sensor to whole blood. The root cause of the problem was identified as a gradual decrease in the rejection properties of the membrane (94) allowing penetration by blood proteins, which fouled the reference. Cellulose acetate was chosen as a shield for the reference electrode due to its barrier properties to proteins and its ability to transport sufficient water and electrolytes to maintain a stable potential at the surface of the printed silver/silver chloride.

The choice of a proper solvent and cure process is critical in preparing a uniform cellulose acetate layer over the reference electrode. The solvent must have a low vapor pressure (high boiling point) in order to provide sufficient screen life for the printing process to be completed. It must be compatible with the printing screens, i.e. not degrade the screen emulsion during printing. The viscosity of the prepared paste must be relatively high, 40,000 centipoise to 350,000 centipoise. This mandates that the % solids of the polymer solution be fairly high, thus the solvent must be very good for the polymer. Suitable solvents include the so-called "super solvents", polar aprotic solvents such as dimethyl formamide, dimethylsulfoxide, hexamethylphosphoramide, and 1,3-dimethyl-2-imidazolidinone (DMI) are examples of this class of solvent. One final restriction was that the solvent not be a carcinogen, mutagen, or teratogen in order that it might be handled more readily by the formulation technician and the screen printer. The preferred solvent is DMI.

Solutions prepared in the concentration range of from 15 to 35 grams of cellulose acetate in 100 mL of DMI were found acceptable for the printing process. The preferred concentration was chosen as 20 grams cellulose acetate in 100 mL of DMI. In order to rapidly dissolve the polymer, the solvent is heated to between 60° and 100° C., with the preferred temperature being 95° C. The polymer is added to the rapidly stirred (magnetic stir bar), heated solvent (water bath with the temperature preset). It is then mechanically mixed in with a spatula, after which it is stirred continuously until completely dissolved. The polymer/solvent mixture (paste) is then removed from the water bath, allowed to cool to room temperature, labeled and set aside until needed for printing.

The paste is generally printed on the same day it is prepared, it can be used up to several months after preparation, however, performance of the layer gradually decreased with paste shelf life. The paste is applied in a 2 pass print after which it is allowed to level for a period of time no less than 10 minutes and no more than one hour. It is cured in a box oven at 55° C. for 10 minutes, the temperature of the oven is then ramped up to 100° C. over a 10 minute period, the curing continues for 10 minutes more at this temperature. This print method/cure cycle is crucial to the performance of the cellulose acetate membrane. Low cure temperatures do not remove sufficient solvent, while longer cures or higher cure temperature lead to a brittle membrane which delaminates easily from the substrate, particularly after post-treatment of the sensor with an anti-drying agent. Printing with more passes leads to a thicker membrane, which is also prone to delamination. It is important not to completely remove solvent, as complete removal would hinder the hydration process.

A layer of cellulose acetate 100 is applied over the silver/silver chloride layer 102 to protect the silver chloride from contaminants present in blood samples that would shift the reference potential. The cellulose acetate layer 100 can be applied by a spotting technique or by a screen printing technique. If the spotting technique is used, an Asymtek XYZ table, available from Asymtek Corporation, Carlsbad, Calif., and known to those of skill in the art, will be used. If a screen printing deposition process is used, a high viscosity solution from a high boiling solvent, such as 2-(2-ethoxyethoxy)ethylene acetate will be used.

Lastly, as noted above, each electrode 86, 88, 90 and 92 is covered with a glucose and oxygen-permeable membrane 94.

Membrane 94 can be formed from cellulose acetate, polyurethane, silicone compounds, and other membrane materials known to those skilled in the art such as Nafion® material available from E. I. DuPont de Nemours, Wilmington, Del. The preferred membrane 94 is a dispersion of a polymerizable silicon-containing compound applied in an incompletely cured form of a silicone compound dispersed phase in a liquid carrier. The carrier is essentially insoluble in the dispersed phase and removable from the dispersion during curing. The dispersion will dry and cure as a continuous layer, film or membrane, having a high glucose and oxygen permeability to function as a single membrane in an electrochemical glucose sensor. A single-layered, semi-permeable membrane is disclosed by Jones, in EP Patent No. 207 370 B1 which is incorporated herein by reference. The silicon-containing compound may be dispersed in the continuous phase as an oligomer, prepolymer, or incompletely cured polymer.

The polymerizable silicon-containing compound, after dispersion in a continuous phase, such as by including an emulsifier, can be cured in any known manner during removal of the continuous phase, such as by evaporation of water from a water-continuous phase silicone emulsion or dispersion, as disclosed by Johnson et al., in U.S. Pat. No. 4,221,688, and Elias, in U.S. Pat. No. 4,427,811, both of which are incorporated herein by reference. Further, the dispersion of the silicon-containing compound can include a suitable curing catalyst, or can be heat cured, so the dispersion of the polymerizable silicon-containing compound is applied as a layer in the form of an incompletely cured dispersion and at least a portion of the carrier or continuous phase is removed from the dispersion during final curing. The emulsion can consist of a dispersion of silicone latex particles and silica. Upon evaporation of water, the silicone latex particles are cross-linked by the silica. The morphology of the resulting membrane is polydiorgano cross-linked particles bounded by a continuum of silica or silicates. It is the silica phase in which analyte transport, i.e. glucose, lactate, etc., takes place.

In accordance with one aspect of the present invention, the polymerizable silicon-containing compound is an organosiloxane, and particularly a diorganosiloxane, comprising essentially a linear species of repeating diorganosiloxane units which may include small numbers of monoorganosiloxane units up to a maximum of about one unit for each 100 diorganosiloxane units wherein the polymer chain is terminated at each end with silicone-bonded hydroxyls.

In accordance with another important aspect of the present invention, the polymerizable silicone-containing compound forming an oxygen and glucose-permeable membrane is applied onto an electrode as an aqueous silicone emulsion comprising a continuous water phase and an anionically stabilized dispersed silicone phase wherein the silicone phase is a graft copolymer of a water soluble silicate and a hydroxyl endblocked polydiorganosiloxane. As disclosed by Saam, in U.S. Pat. No. 4,244,849, incorporated herein by reference, such silicone emulsions, having a pH within the range of from about 8.5 to about 12.0, are stable upon extended storage and result in a cured elastomeric continuous layer upon removal of water under ambient conditions. These silicone compounds are obtained from the interaction of hydroxyl endblocked polydiorganosiloxanes and alkali metal silicates to form graft polymers anionically stabilized in aqueous emulsions at pH of, for example, 8.5 to 12.0. If stability is not important, however, the pH is not critical. The emulsion can be applied in layer form to manufacture the membrane as soon as the components are homogeneously dispersed.

The expression "hydroxyl endblocked polydiorganosiloxane" is understood to describe an essentially linear polymer of repeating diorganosiloxane units containing no more than small impurities of monoorganosiloxane units. The hydroxyl endblocked diorganosiloxane will therefore have essentially two silicon-bonded hydroxyl radicals per molecule. To impart elastomeric properties to the product obtained after removal of the water from the emulsion, the polysiloxane should have a weight average molecular weight ($M_w$) of at least 5,000. Polysiloxanes with weight average molecular weights below about 5,000 down to about 90, also are useful if the polymers form a continuous film or layer upon curing. Tensile strengths and elongations at break improve with increasing molecular weight, with relatively high tensile strengths and elongations obtained above 50,000 $M_w$. However, since in a preferred embodiment of the invention, the cured polymers are bonded directly to an electrode, and do not undergo any severe mechanical stress during use, high strength is not necessary for the polymer to be useful. The maximum $M_w$, is one which can be emulsified or otherwise dispersed in a liquid carrier or continuous phase, such as water. Weight average molecular weights up to about 1,000,000 for the incompletely cured dispersed polysiloxane are practical for use in the sensor of the present invention. Upon curing, there is no upper limit to the molecular weight of the membrane. The preferred $M_w$ for the polymerizable dispersed siloxane is in the range of 1,000 to 700,000.

Organic radicals on useful hydroxyl endblocked polydiorganosiloxanes can be, for example, monovalent hydrocarbon radicals containing less than seven carbon atoms per radical and 2-(perfluoroalkyl)ethyl radicals containing less than seven carbon atoms per radical. Examples of monovalent hydrocarbon radicals include methyl, ethyl, propyl, butyl, isopropyl, pentyl, hexyl, vinyl, cyclohexyl and phenyl; and examples of 2-(perfluoroalkyl)ethyl radicals include 3,3,3-trifluoropropyl and 2-(perfluorobutylmethyl). The hydroxyl endblocked polydiorganosiloxanes preferably contain organic radicals in which at least 50 percent are methyl. The preferred polydiorganosiloxanes are the hydroxyl endblocked polydimethylsiloxanes.

In accordance with one important aspect of the present invention, the hydroxyl endblocked polydiorganosiloxane is employed as an anionically stabilized aqueous emulsion. For the purposes of this embodiment "anionically stabilized" means the polydiorganosiloxane is stabilized in emulsion with an anionic surfactant. The most preferred anionically stabilized aqueous emulsion of hydroxyl endblocked polydiorganosiloxane are those prepared by the method of anionic emulsion polymerization described by Findlay et al., in U.S. Pat. No. 3,294,725, hereby incorporated herein by reference. Another method of preparing hydroxyl endblocked polydiorganosiloxanes is described by Hyde et al., in U.S. Pat. No. 2,891,920, also incorporated herein by reference.

An alkali metal silicate or colloidal silica must be included in the emulsified silicone composition for the preparation of extended storage stable emulsions used in the invention. The alkali metal silicates preferred for use in the emulsions forming the oxygen and low molecular weight analyte-permeable membranes of the present invention are water soluble silicates. The alkali metal silicate is preferably employed as an aqueous solution. Aqueous silicate solutions of any of the alkali metals can be employed, such as lithium silicate, sodium silicate, potassium silicate, rubidium silicate and cesium silicate.

The colloidal silicas are well known in the art and commercially available, and can be included in the dispersion for increased strength and storage stability. Although any of the colloidal silicas can be used, including fumed and precipitated colloidal silicas, silicas in an aqueous medium are preferred. Colloidal silicas in an aqueous medium are usually available in a stabilized form, such as those stabilized with sodium ion, ammonia or an aluminum ion. Aqueous colloidal silicas which have been stabilized with sodium ion are particularly useful for forming an emulsion because the pH requirement can be met without having to add other components to bring the pH within the range of, for example, 8.5 to 12.0. The expression "colloidal silica" as used herein are those silicas which have particle diameters of from about 0.0001 to about 0.1 micrometers. Preferably, the particle diameters of the colloidal silicas are from about 0.03 to about 0.08 micrometers; most preferably, the silica particle diameter is about 0.06 micrometers.

The colloidal silica can be added to the anionically stabilized hydroxylated polydiorganosiloxane in the form of a dry powder or as an aqueous dispersion. Preferably, the colloidal silica is added in the form of a sodium ion stabilized aqueous dispersion of colloidal silica, many of which are commercially available. These commercial colloidal silicas are usually available in aqueous dispersions having between about 10.0 to about 30.0 percent, by weight, colloidal silica, and a pH between about 8.5 to about 10.5.

Aqueous solutions of sodium or potassium silicate are well known and are commercially available. The solutions generally do not contain any significant amount of discrete particles of amorphous silica and are commonly referred to as water glass. The ratio, by weight, of silica to alkali metal oxide in the aqueous solutions of alkali metal silicates is not critical and can be varied between about 1.5 to about 3.5 for the sodium silicates, and about 2.1 to about 2.5 for the potassium silicates. The aqueous alkali metal silicate solutions are particularly useful in preparing the emulsions used in the present invention because the addition of the silicate solution often brings the pH of the emulsion within the range of about 8.5 to about 12.0 so that additional ingredients are not necessary to adjust the pH of the emulsion. Of course, other aqueous alkali metal silicate solutions, such as those prepared by hydrolyzing silicon esters in aqueous alkali metal hydroxide solutions, can also be employed in the present invention.

In accordance with one aspect of the present invention, the polymerizable silicon-containing compound is dispersed by combining an aqueous solution of an alkali metal silicate and the polymerizable silicon-containing compound in an emulsion so that a graft copolymer is formed as dispersed particles. The preferred procedure for preparing silicone emulsions is to add the alkali metal silicate to an anionically stabilized aqueous emulsion of one or more hydroxyl endblocked polydiorganosiloxanes, adjust the pH of the emulsion within the range of about 8.5 to about 12.0, and then age the emulsion for a period to form an elastomeric product upon removal of the water under ambient conditions. In this procedure, the pH of the emulsion containing dissolved silicate and dispersed hydroxyl endblocked polydiorganosiloxane is important to the formation of the emulsion. A pH of 8.5 to 12.0 maintains the alkali metal silicate dissolved so that sufficient graft copolymerization between the dissolved silicate and dispersed siloxane occurs during removal of the carrier (e.g., water) to produce an emulsion capable of providing polymerization, or further polymerization, of the silicon-containing compound when deposited as a layer to form a membrane. If the pH is lower than the stated range, silicic acid is formed from the alkali metal silicate. Silicic acid is unstable and rapidly polymerizes by condensation, which can gel the emulsion. Since silicic acid formation is almost completely suppressed at a pH of between about 10.0 to about 12.0, and the reaction between dissolved alkali metal silicate and dispersed siloxanes occurs more rapidly within this pH range, this range is preferred for emulsions containing an alkali metal silicate.

Silicone emulsions prepared by silicate copolymerization are aged at a pH range of between about 8.5 to about 12.0 for a period sufficient to allow interaction between the dissolved silicate and the dispersed siloxane so that an elastomeric product is formed upon removal of the water under ambient conditions. The aging period is effectively reduced when an organic tin salt is employed in an amount between about 0.1 to about 2.0 parts, by weight, of polydiorganosiloxane. The organic tin salts expected to be useful in the emulsions include mono-, di- and triorganotin salts. The anion of the tin salt employed is not critical and can be either organic or inorganic, although organic anions such as carboxylates are generally preferred. Organic tin salts that can be employed include octyltin triacetate, dioctyltin dioctoate, didecyltin diacetate, dibutyltin diacetate, dibutyltin dibromide, dioctyltin dilaurate and trioctyltin acetate. The preferred diorganotin dicarboxylate is dioctyltin dilaurate.

The relative amounts of alkali metal silicates and hydroxyl endblocked polydiorganosiloxane employed can vary over a considerable range. Preferred elastomer properties are obtained when between about 0.3 to about 30 parts, by weight, silicate is employed for each 100 parts, by weight, siloxane.

In accordance with one aspect of the invention, an alkyl tin salt is added to the dispersion to catalyze the curing of the final emulsion during the devolatization, or other removal, of the carrier to yield the cured membrane. Preferred salts are dialkyltin dicarboxylates such as dibutyltin diacetate, dibutyltin dilaurate, and dioctyltin dilaurate; the most preferred tin salt is dibutyltin dilaurate. The emulsion of catalyst is used in an amount sufficient to yield between about 0.1 to about 2.0 parts, by weight, of the alkyl tin salt for each 100 parts, by weight, of the polymerizable silicon-containing compound, such as polydiorganosiloxane. Larger amounts could by used, but would serve no useful purpose.

The dispersion of the polymerizable silicon-containing compound(s) can contain components in a broad range of concentrations. The preferred concentrations will depend on the thickness of the membrane desired. For example, to provide a thin elastomeric membrane (20 microns) that does not form cracks as the carrier or continuous phase evaporates, it is best to use a dispersion having a combined amount of silicate and polydiorganosiloxane in the range of between about 67.0 to about 160.0 parts, by weight, for each 100 parts, by weight, of carrier such as water. Preferred membrane thicknesses are between about 10.0 to about 100.0 microns, preferably about 20.0 microns.

If an emulsifying agent is incorporated into the composition to form the dispersion the amount of emulsifying agent can be less than about 2.0 percent, by weight, of the emulsion. The emulsifying agent can result from neutralized sulfonic acid used in the emulsion polymerization method for the preparation of a hydroxyl endblocked polydiorganosiloxane.

Anionic surfactants are preferably the salts of the surface active sulfonic acids used in the emulsion polymerization to form the hydroxyl endblocked polydiorganosiloxane. The alkali metal salts of the sulfonic acids are preferred, particularly the sodium salts. The sulfonic acid can be illustrated by aliphatically substituted benzenesulfonic acids, naphthalene sulfonic acids, and diphenylether sulfonic acids, aliphatic sulfonic acids, and silylalkylsulfonic acids. Other anionic emulsifying agents can be used, for example, alkali metal sulforicinoleates, sulfonated glyceryl esters of fatty acids, salts of sulfonated monovalent alcohol esters, amides of amino sulfonic acid such as the sodium salt of oleyl methyltauride, sulfonated aromatic hydrocarbon alkali salts such as sodium alpha-naphthalene monosulfonate, condensation products of naphthalene sulfonic acids with formaldehyde, and sulfates such as ammonium lauryl sulfate, triethanol amine lauryl sulfate and sodium lauryl ether sulfate.

Nonionic emulsifying agents can also be included in the emulsion (in addition to the anionic emulsifying agents). Such nonionic emulsifying agents are, for example, saponins, condensation products of fatty acids with ethylene oxide such as dodecyl ether of tetraethylene oxide, condensation products of ethylene oxide and sorbitan trioleate, condensation products of phenolic compounds having side chains with ethylene oxide, such as condensation products of ethylene oxide with isododecylphenol, and imine derivatives such as polymerized ethylene imine.

The polymerizable silicon-compound dispersion used to form the oxygen and glucose-permeable membranes of the present invention may contain additional ingredients to modify the properties of the dispersions, or the cured polymeric membrane products obtained from the dispersions. For example, a thickener may be added to modify viscosity of the dispersion or to provide thixotropy for the dispersion. An antifoam agent may be added to the dispersion to reduce foaming during preparation, coating or curing in layer form.

Fillers may be added to the dispersion to reinforce, extend or pigment the membrane. Useful fillers include colloidal silica, carbon black, clay, alumina, calcium carbonate, quartz, zinc oxide, mica, titanium dioxide and others well known in the art. These fillers should be finely divided and it may be advantageous to use aqueous dispersions of such fillers.

The filler preferably has an average particle diameter of less than about 10.0 micrometers. When the silicone emulsions are spread out for final curing to form the oxygen and glucose-permeable membranes of the present invention, the water, or other nonsolvent carrier, evaporates, or is otherwise removed, to leave a cured oxygen and glucose-permeable membrane. Evaporation of the carrier is usually complete within a few hours to about one day depending on the dispersion film thickness and method of application. Another of the important advantages of the present membrane is excellent adhesion to both polar and nonpolar substrates.

One of the more important advantages of the oxygen and analyte-permeable membranes used with the present invention, is the capability of these membranes to be bonded to an electrode activated with a suitable enzyme catalyst, such as glucose oxidase, glucose dehydrogenase or lactate oxidase. In accordance with one embodiment of the present invention, a compound capable of catalyzing the reaction of glucose with oxygen is incorporated within the anode, or active layer 96, and the oxygen and glucose-permeable membrane 94 of the present invention is coated over the reference, counter, working (including active layer 96), and interference correcting electrodes 86, 88, 90, and 92.

The membrane materials described herein are very compatible with whole blood 98, have a durable surface and are highly selective to oxygen penetration so that a sufficient stoichiometric excess of oxygen permeates the membrane 94 even from whole blood.

The preferred materials for membrane 94 are an anionically stabilized, water-based hydroxyl endblocked polydimethylsiloxane elastomer containing at least about 10.0 percent silica, by weight. Most preferably, the elastomer contains about 14.0 percent, by weight, colloidal silica, and is commercially available as FC-61 coating from Dow Corning, Midland, Mich. This material is a low viscosity, filled, opaque emulsion. Typically, this material has a pH of about 11.0, and a viscosity of about 40,000 cp.

In another aspect of the present invention, it has been found that during dry storage of sensors 28, membranes 94 become increasingly more difficult to wetup. It is believed that residual water and other solvents, initially present in the membrane 94 after casting, evaporate during storage and cause coalescence of silicone agglomerates. This tightening of the membrane structure can decrease the sensitivity and increase the response time of the sensor toward glucose.

The sensors 28 can be post-treated to prevent the membrane from aging during dry storage, for example, by preventing the membranes from fully drying with humidification, or treatment with a high boiling point, water soluble, hydrophilic polymer liquid antidrying agent, such as surfactants or polyethylene glycols. Preferably, a non-ionic surfactant, having a molecular weight of at least about 300, such as Triton® X-100 surfactant, Tergitol® 15 surfactant from Union Carbide Chemicals and Plastics Co., Inc., Danbury, Conn., Tween® 20 ethoxylated sorbitan esters surfactant from ICI Surfactants, Wilmington, Del., and polyethylene glycols having molecular weights between about 200 and 600, are applied for post-treatment of sensors 28 to improve output, and response time, while minimizing sensor drift, upon initial start-up. The preferred material for post-treatment is polyethylene glycol having a molecular weight of about 400.

Referring again to FIGS. 9A and 9B, while noting that a variety of sensor configurations can be advantageous in different applications, the following non-limiting preferred dimensional specifications of a sensor 28 fabricated in accordance with a preferred embodiment of the present invention are given.

Substrate 62 can be fabricated in a variety of shapes and sizes. According to one specific preferred embodiment of the invention, substrate 62 is from about 0.4 inch to about 0.5 inch long; preferably, about 0.45 inch long. Substrate 62 is from about 0.15 inch to about 0.25 inch wide; preferably, about 0.18 inch wide. Substrate 62 is from about 0.02 inch to about 0.05 inch thick; preferably, about 0.025 inch thick. Conductive strips 64, 66, 68 and 70 are each deposited in a thickness of from about 10.0 microns to about 20.0 microns; preferably, the strips are about 15.0 microns thick. Conductive strips 64, 66, 68, and 70, at end 76 of the sensor, are from about 0.01 inch to about 0.03 inch wide, preferably about 0.01 wide. Contact pads 78, 80, 82, and 84 at end 74 of the sensor, are from about 0.025 inch to about 0.05 inch wide, preferably about 0.03 inch wide.

Dielectric layer 72 is preferably deposited in a thickness of from about 10.0 microns to about 50.0 microns, preferably about 20.0 microns thick. Thickness values are given after firing or curing.

Portions of the conductive strips are exposed to define the reference electrode 86, counter electrode 88, working electrode 90, and interference correcting electrode 92. The exposed surface area for the reference electrode 86 is about 0.00015 inch$^2$, and for the counter electrode 88 is about 0.00022 inch$^2$. The working and interference correcting electrodes 90, 92, each have surface areas of about 0.00038 inch$^2$. These exposed surface area dimensional specifications do not take into consideration surface area due to the edges of the electrodes, defined by the thickness of the electrodes as deposited or the porosity of the layer. Such edge dimensions are minimal relative to the overall electrode areas. However, the exposed surface area specification are thus somewhat approximate.

A cellulose acetate layer 100 is applied over the silver/silver chloride layer 102 of the reference electrode 86, which was deposited over the exposed portion of conductive strip 68. The cellulose acetate layer 100 protects the silver chloride from contaminates that would shift the reference potential.

The active and inactive layers are then applied over the exposed portions of conductive strips 66 and 70, forming the working and interference correcting electrodes 90, 92, respectively.

Cover membrane 94 is then deposited, preferably spun-cast, to a total thickness from about 5.0 microns to about 50.0 microns, preferably from about 10.0 microns to about 20.0 microns. The cover or protective membrane 94 is preferably applied in layers to enable thin overall thickness with required permeability characteristics.

The present invention will be further illustrated by the following examples which are intended to be illustrative in nature and are not to be construed as limiting the scope of the invention.

EXAMPLE I

Figure 9B:
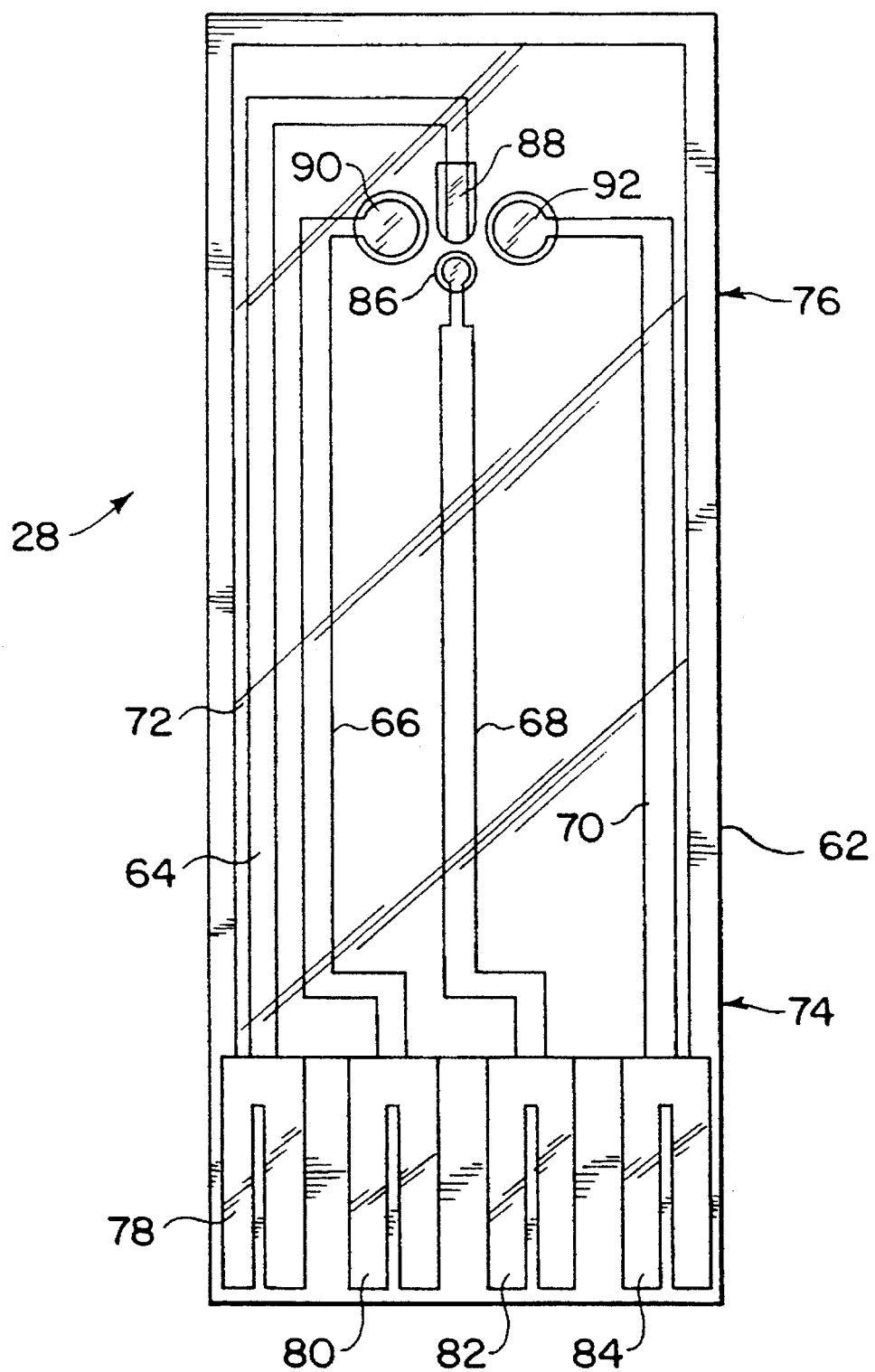
FIG. 9B is a magnified top plan view of another embodiment of a sensor used in the sensor package shown in FIG. 1.

Referring to FIGS. 9 and 9B and 25 and Table I, one suitable construction of a solid state, planar glucose sensor 28 including the components and design substantially in accordance with an aspect of the present invention is provided by the following combination of elements.

A partial assembly of planar glucose sensor 28 having substrate 62 and conductive metal strips 64, 66, 68 and 70 was fabricated in accordance with a method of the present invention on a 0.025 inch thick, 0.18 inch by 0.45 inch, electrically nonconducting substrate 62 comprising approximately 96% alumina and approximately 4% glass binder, available from Coors Ceramic Company, Grand Junction, Colo. Portions of conductive strips 64, 66, 68 and 70, as well as contact pads 78, 80, 82 and 84, were deposited onto the substrate using a screen printing technique, with a 10.0 micron emulsion of gold conductor paste, available as product number PC10231 from Metech, Inc., Elverson, Pa. A stainless steel screen having a 325 mesh pattern was used to screen print the gold paste onto substrate 62. Conductor strips 64, 66 and 70 were connected with platinum upper portions, as the conductive strips were continued toward second end 76. These strips were fabricated by screen printing a 10.0 micron emulsion high purity platinum conductor paste, available as product number PC10208 from Metech, onto the substrate. A screen similar to that described above was used to deposit the platinum conductor composition. Conductor strip 68 was similarly continued toward second end 76 by applying a 10.0 micron emulsion silver conductor paste, available as product number 3571UF from Metech, onto the substrate. The 325 mesh screen made of stainless steel wire was used to screen print the silver conductor paste. A 10.0 micron emulsion silver/silver chloride reference electrode ink, available as product number 2539 from Metech, was subsequently screen printed over a portion of conductive strip 68 at end 76, covering an area of conductive strip 68 at least as large as, and preferably larger than, the area of conductive strip 68 to be exposed by dielectric layer 72 to define reference electrode 86. Lastly, a cellulose acetate layer 100, available as product number 18095-5 from Aldrich Chemical Co., Milwaukee, Wis., was screen printed over the silver/silver chloride reference electrode 86. This layer is applied over the reference electrode to protect the silver chloride from contamination that could shift the reference potential.

In this example a BTU 7 zone furnace with a 3 zone dryer, from Fast Fire of Billerica, Mass., was used in firing the inorganic pastes. Firing was carried out per the manufacturer's recommendations, ramped to the peak conditions. The gold conductor paste was fired at 850° C. for a 10 minute peak, the platinum conductor paste was fired at 750° C. for a 13 minute peak, and the silver conductor ink was fired at 750° C. for a 10 minute peak.

Conductive strips 64, 66, 68 and 70 were deposited on substrate 62 so as to be 0.01 inch wide at end 76; contact pads 78, 80, 82 and 84 were deposited on substrate 62 so as to be 0.03 inch wide, and 0.8 inch long at end 74.

A dielectric material 72, available as product number 9615 from DuPont Electronics, Wilmington, Del., was screen printed as a 15.0 micron emulsion over a large portion of sensor 28, extending from second end 76 to contact pads 78, 80, 82 and 84. A 325 mesh screen made of stainless steel was used for the screen printing process. The dielectric was fired at 750° C. for a 10 minute peak. As noted above, portions of conductive strips 64, 66, 68 and 70 were not covered by dielectric 72, exposing their electrode areas.

Silver/silver chloride is applied at 75° C. for 30 minutes.

Cellulose acetate is applied at 55° C. for 10 minutes, ramped to 100° C. for 10 minutes, and then 10 minutes at 100° C. (30 minute cure time).

An active layer 96, comprising a catalytically active quantity of glucose oxidase, available from Biozyme Laboratories International, Ltd., San Diego, Calif., immobilized onto platinized carbon powder particles, available from E-TEK, Inc., Framingham, Mass., was deposited upon conductive strip 66 to form working electrode 90 also using a thick film screen printing technique. An inactive layer, comprising an inactive protein, such as bovine serum albumin, sold under the trademark Pentex® bovine albumin from Miles, Inc., Kankakee, Ill., immobilized onto platinized carbon powder particles, available from E-TEK, was deposited upon conductive strip 70 to form interference correcting electrode 92 using similar thick film screen printing techniques. The fabrication of the active and inactive layers is described in further detail in Example II.

After the conductive strips, dielectric layer, and electrodes are deposited onto substrate 62 and the contact are masked to prevent electrode "shunting", a cover membrane 94 is spun-cast over the electrode area of the sensor. An anionically stabilized, water-based hydroxyl endblocked polydimethylsiloxane elastomer, comprising about 14 percent, by weight, colloidal silica, commercially available as Fabric Coating (FC)-61 from Dow Corning, Midland, Mich., was applied to the sensor 28 using a spin-casting technique. An IVEK laboratory pump and an Integrated Technologies P-6000 spin coater were used to apply the cover membrane 94 in multiple layers over the sensor. The first layer was applied by complete flooding of the wafer with the membrane elastomer material. The Integrated Technologies P-6000 spin coater was then activated to a spin speed of 7,000 rpm, and a spin time of 90 seconds. After the spinning was completed, the first layer was allowed to dry for 15 minutes. The sensor 28 was then spun again at 7,000 rpm, and the second layer of the membrane material was applied. Two additional layers were applied using the spin/flood technique used to apply the second layer, allowing 15 minutes between casting each layer. After all four layers have been cast, the membrane 94 was cured overnight at room temperature in a dust-free environment. The total thickness of the multiple layers of membrane 94, after curing, is approximately 20.0 microns.

EXAMPLE II

Active layer 96 was prepared for use in working electrode 90 (as noted in Example I). The active layer 96, for a glucose sensor, primarily includes a catalytically active quantity of glucose oxidase, available from Biozyme Laboratories, immobilized onto platinized carbon powder particles, available from E-TEK, and the particles are distributed substantially uniformly throughout the layer.

About 3.15 grams of platinized carbon powder particles, Vulcan® XC-72 carbon black, available from Cabot Corporation, Boston, Mass., prepared by the deposition of colloidal platinum (particle size between about 1.5 to 2.5 nm) onto the surface of the carbon powder (nominal particle size about 30 nm) by oxidative decomposition of complex platinum sulfite acid (II) using $H_2O_2$, were treated in a phosphate buffer to neutralize any residual sulfuric acid present. The phosphate buffer also includes a microbicide, sold under the trademark Kathon® CG microbicide of Rohm & Haas Corp., Philadelphia, Pa. The buffer was prepared by adding 11.499 grams sodium phosphate, dibasic ($Na_2HPO_4$), 2.898 grams sodium phosphate, monobasic monohydrate ($NaH_2PO_4"H_2O$), and 1.0 gram of the Kathon® CG microbicide to 1.0 liter of distilled water. The buffer formulation was tested using a pH meter and electrode, to have a pH of 7.5. Approximately 100 ml of the phosphate buffer was added to the 3.15 grams of platinized activated carbon, and was mixed for 7 days. The buffer was replaced after the first 3 days of mixing by allowing the platinized activated carbon to settle, decanting off 60 ml of the used buffer, and replacing it with 100 ml of fresh buffer. The mixture was then vacuum filtered after the 7 days of mixing, and the neutralized carbon was washed while under vacuum filtration using 100 ml of buffer. The vacuum was maintained for about 15 to 20 seconds after the bulk of the buffer had been pulled through the carbon to slightly dry the carbon and improve handling of the material.

The platinized activated carbon (PAC) was then mixed with 625 mg of Pentex® bovine serum albumin (BSA). The 625 mg of BSA was first added to a flask containing the PAC and an additional 40 ml of buffer. The BSA and PAC were gently mixed with a laboratory rotator and allowed to sit for ½ hour to permit the BSA to dissolve. The mixture was again gently mixed overnight at a speed setting of 3.5 for approximately 18 hours at room temperature. The BSA-PAC mixture was then vacuum filtered and washed under the vacuum filtration with 100 ml of buffer. Again, the vacuum was applied for about 20 seconds after the bulk of the buffer was pulled through the BSA-PAC to dry the BSA-PAC to between about 60 to 70 percent moisture. The BSA-PAC was then refrigerated for future use in the active and inactive layer inks for screen printing.

The active layer ink was formulated by adding 5.0 grams of a binder resin, available as product number 8101 RS from Metech, to 2.0 grams of the BSA-PAC (as prepared above). To this mixture, 0.25 gram of Triton® X-100 surfactant was added as a printing flow aid and wetting agent for the layer. The mixture was then milled using a standard paint industry three roll mill. 1.0 ml of AlbessoT thinner, available from Metech as 8101 RS thinner, was added to the mixture, after the first milling was completed to adjust the viscosity of the paste for printing purposes. The mixture was then milled for a second period. Lastly, 0.4 gram of glucose oxidase, available from Biozyme Laboratories, was added and milled into the mixture. The active paste was then screen-printed onto conductive strip 66 electrode portion to form working electrode 90.

EXAMPLE III

An inactive layer ink, used to form the interference correcting electrode 92, was formulated using the procedure set forth in Example II. The inactive layer, however, does not include any catalytically active quantity of an enzyme such as glucose oxidase. The inactive layer ink was prepared by milling 5.0 grams of binder resin with 2.0 grams of BSA-PAC (as prepared in Example II), 0.25 gram of Triton® X-100 surfactant and 1.0 ml of AlbessoT (8101 RS) thinner.

To this mixture an additional 0.4 gram of Pentex® BSA was added and milled. Inactive layer paste was then screen-printed onto conductive strip 70 electrode portion to form interference correcting electrode 92.

EXAMPLE IV

Referring again to FIGS. 1 through 8, one suitable construction of a sensor package 10 including the components and design substantially in accordance with an aspect of the present invention is provided by the following combination of elements.

Sensor package 10 is molded of V825 acrylic plastic, available from Rohm & Haas Corp., and includes an open back J-body, having a width of about 0.5 inch, a main body 14 length of about 1.535 inches, and a thickness of about 0.37 inch. A handle 12, or gate portion, extends from the main body for aiding the insertion or removal of the sensor package 10 into or from an instrument. The package 10 includes a housing 20 having a substantially oval-shaped recess 22 formed therein. The recess has a length of about 0.1 inch and a width of about 0.065 inch. The recess includes an outer perimeter 24 and a passageway 18 made up of an inlet 56 and outlet 58. The passageway enters and exits recess 22 lengthwise. Passageway 18 has a substantially circular cross-section and a diameter of approximately 0.03 inch. As shown in FIGS. 5–8, a velocity compensator or bump 60 is provided in the recess 22. Velocity compensator 60 traverses the width of recess 22, and is approximately 0.065 inch in length and about 0.04 inch in width. The velocity compensator 60 is a bump-like protrusion in passageway 18 which has a radius of about 0.02 inch. The velocity compensator reduces the internal volume of the sample chamber and creates a cross-sectional area close to the inlet 56 and outlet 58 diameters. A gasket 26 is then provided to contact, and form a seal between, the housing recess perimeter 24 and a sensor 28 (as prepared in Example I). Gasket 26 is made from SarlinkT 2450 elastomer having a hardness of about 50 on the Shore A scale. Gasket 26 is square-shaped, having sides of about 0.17 inch. Gasket 26 further includes a substantially oval-shaped opening having a length of about 0.1 inch and a width of about 0.064 inch.

Gasket 26 is approximately 0.014 inch thick at its central cavity portion and approximately 0.05 inch thick at two outer sides along the length of the gasket opening. These thicker surfaces allow the gasket to fit around the housing recess perimeter, while also allowing the recess 22 to be open to the sensor electrode area to form a sensor sample chamber.

As noted in Example I a solid state, planar electrochemical sensor is formed on a ceramic substrate of about 0.025 inch thickness, and 0.45 inch length and 0.18 inch width. The sensor 28 is placed upon a base pad made of a silicone rubber material having a hardness of between about 40 to 60 on the Shore A scale. The pad has a length of about 0.5 inch and a width of about 0.227 inch. The base pad 30 has a total thickness of about 0.058 inch, including a series of transverse protrusions on the rear side thereof which extend about 0.015 inch from the base pad rear surface and are spaced about 0.1 inch apart. The base pad 30 also includes a central rectangular-shaped cavity on the opposite side thereof for receipt of sensor 28. The cavity is about 0.45 inch long and about 0.185 inch wide.

Lastly, a contact lead frame 32 is provided to connect sensor 28 to an instrument which can measure and convert the current to determine the glucose (or lactate) concentration in the sample. Lead frame 32, also shown in FIGS. 3 and 4, includes four leads 34, each approximately 0.041 inch wide at a base end and about 0.026 inch wide at the lead contacts 50. The leads are approximately 1 inch in length and approximately 0.01 inch thick. The leads 34 are made from a BeCu alloy material, which is nickel plated to a thickness of between about 40 to 80 microinches, and gold plated with a microelectronic grade gold plate material to a thickness of between about 20 to 50 microinches thickness.

The lead frame 32, also molded of V825 acrylic plastic, includes the leads secured to a base 36 at a first end portion 38, and a sensor recess 40 at a second end portion 42. The sensor recess 40 is about 0.042 inch deep, approximately 0.5 inch in length, and about 0.225 inch in width, for receipt of the base pad 30 and sensor 28. Lead frame 32 includes a second rectangularly-shaped recess 46 that is about 0.06 inch deep, about 0.296 inch in length, and about 0.085 inch in width. The second recess 46 is for receipt of a stabilizer bar 44, which aligns the leads 34 with the sensor contact pads (described above). The stabilizer bar 44 is a rectangular-solid shaped piece, also molded of the V825 acrylic plastic material from Rohm & Haas Corp. The stabilizer bar is approximately 0.29 inch in length and 0.075 inch in width and height.

After the base pad 30 and sensor 28 are placed into the sensor recess 40, leads 34 are bent around frame 32 until leads 34 come into contact with the sensor, and the stabilizer bar 44 is secured in recess 46. The lead frame is approximately 1.147 inches in length and about 0.395 inch in width. After the components including the gasket 26, sensor 28, base pad 30 and contact lead frame 32 are assembled, the housing and lead frame are secured together by an ultrasonic weld around the outer periphery of the contact lead frame. Four instrument electrical contact surfaces 52 are exposed after the sensor package 10 is assembled. The contact surfaces are spaced between three dividers which extend past lead frame first end 38 about 0.064 inch, and are about 0.1 inch long and 0.033 inch wide. Instrument contact surfaces 52 have about 0.1 inch exposed for electrical contact with an instrument.

EXAMPLE V

Figure 12:
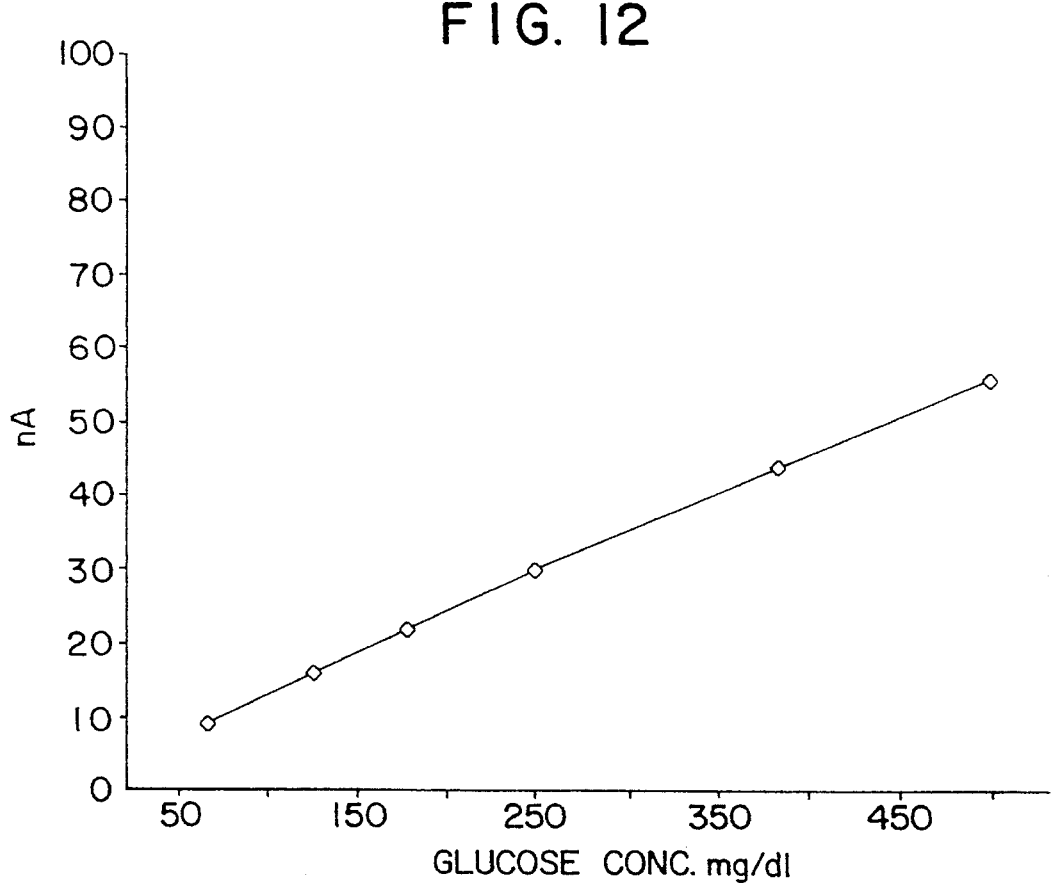
FIG. 12 is a graphical illustration of a glucose sensor response to glucose concentration in whole blood samples according to one embodiment of the present invention.

A planar glucose sensor, constructed substantially in accordance with EXAMPLES I–IV, was evaluated with whole blood, and the relationship between glucose concentration in mg/dl and sensor current in nanoamperes (nA) was plotted as shown in FIG. 12. One of the significant features of the sensor, as graphically illustrated in FIG. 12, is the linear relationship of glucose concentration to sensor current. It is believed that the sensor membrane 94, being both glucose and oxygen-permeable, allows a stoichiometric excess of oxygen to glucose to permeate the membrane from whole blood resulting in the linear relationship from the low end to the high end of the graph.

Figure 13:
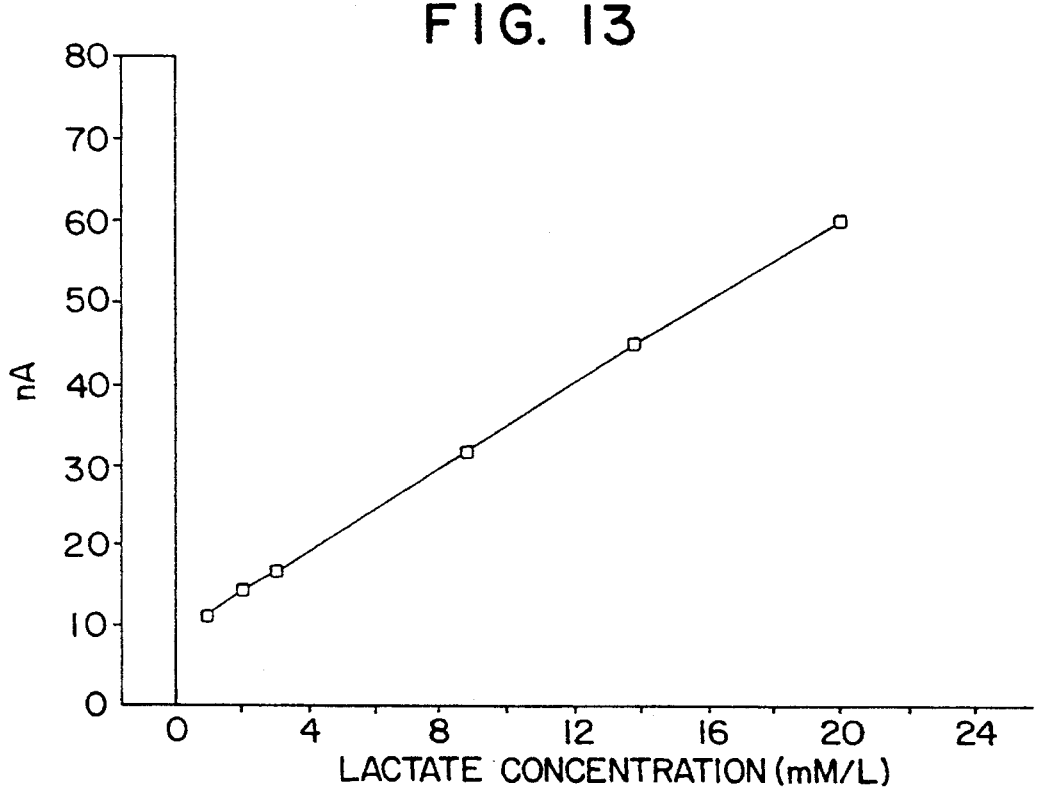
FIG. 13 is a graphical illustration of a lactate sensor response to lactate concentration in whole blood samples according to one embodiment of the present invention.

A similar sensor was evaluated to determine the response to lactate in whole blood. The sensor used was substantially equivalent to that constructed in EXAMPLES I–IV, with the exception of the use of lactate oxidase instead of glucose oxidase. The relationship between the lactate concentration in mmoles/L and sensor current in nanoamperes (nA) was plotted in FIG. 13. One of the significant features of the sensor, as graphically illustrated in FIG. 13, is the linear relationship of lactate concentration to sensor current. Once again, it is believed that the membrane, being both lactate and oxygen-permeable, allows a stoichiometric excess of oxygen to lactate to permeate the membrane from whole blood resulting in the linear relationship from the low end at about 1.00 mmoles/L to the high end of the graph at about 20.0 mmoles/L lactate.

EXAMPLE VI

Figure 14:
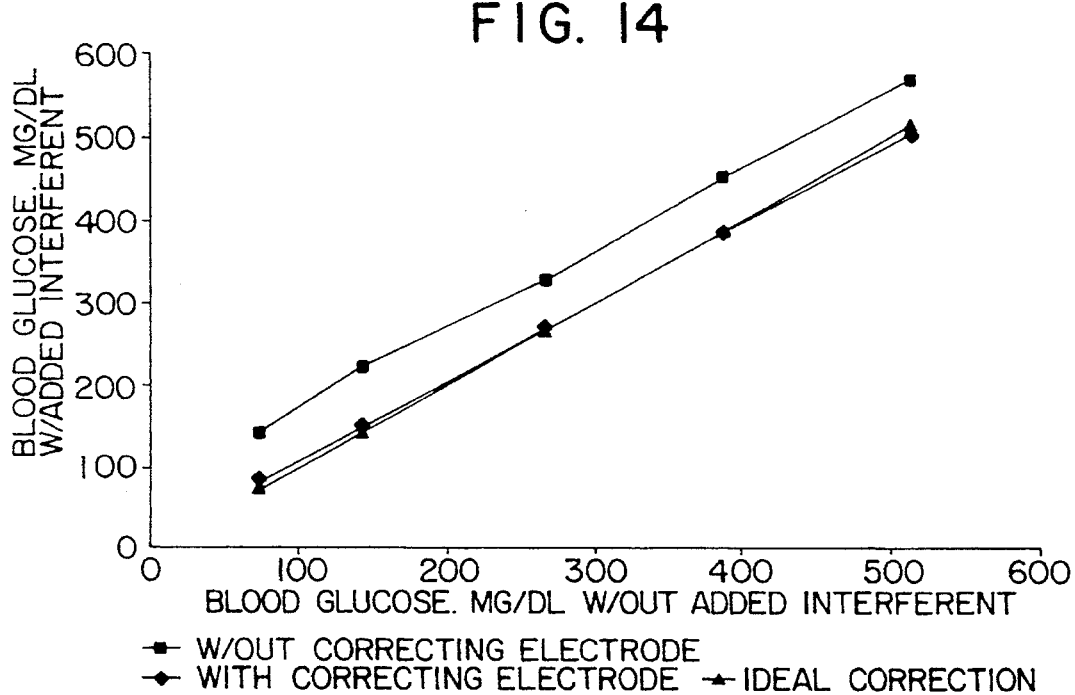
FIG. 14 is a graphical illustration of the effect of an interference correcting electrode according to one embodiment of the present invention, as glucose concentrations are measured with and without the correcting electrode applied.

To determine the effect of the interference correcting electrode 92, a glucose sensor response to glucose concentration, with and without the correcting electrode applied, was recorded as graphically illustrated in FIG. 14. Electrode 92 is provided to adjust for any interfering species, such as the neutral species acetaminophen, which can diffuse through the sensor's semi-permeable membrane 94.

In this example, 1.0 mmole/L of an interfering substance (acetaminophen) was added to a series of blood samples, covering a range of glucose concentrations up to 500.0 mg/dl. As noted, the data are shown in FIG. 14 with and without the correcting electrode applied. Without the correcting electrode, there is approximately a 65.0 mg/dl positive offset from the case where the interference correcting electrode is applied. In other words, if the interference correcting electrode is not used, a mean error of +65.0 mg/dl is obtained over the range of glucose concentrations. This is enough to cause a normal blood glucose level of about 82.0 mg/dl to read outside of the normal range, to about 147.0 mg/dl if left uncorrected.

The glucose sensor response with the correcting electrode applied shows excellent correlation with the ideal correction.

EXAMPLE VII

Figure 15:
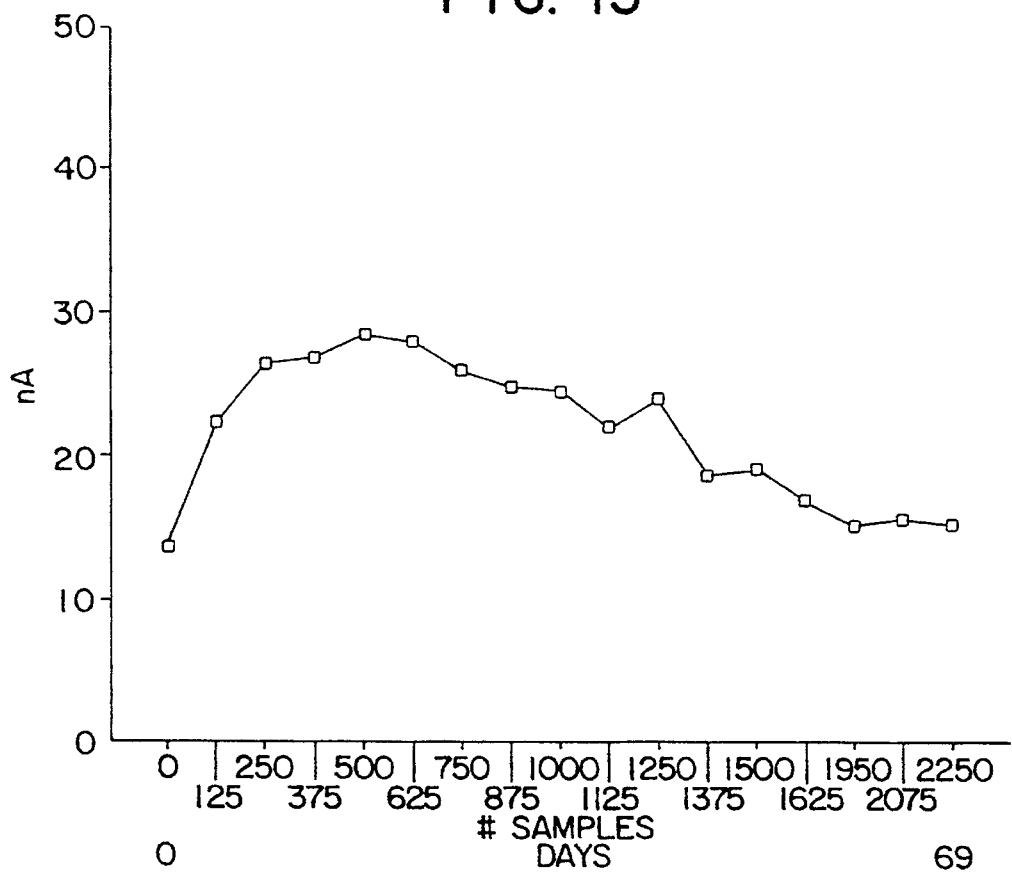
FIG. 15 is a graphical illustration of a glucose sensor output over an extended period of time and sample use.

To determine the lifetime of the present electrochemical sensors, a glucose sensor, constructed substantially in accordance with EXAMPLES I–IV, was used over an extended sampling period, and for a large number of samples. The sensor was tested over a period of sixty-nine (69) days, wherein a total of two thousand two hundred fifty (2,250) samples were evaluated. The current in nA for an aqueous solution having a glucose concentration of 180 mg/dl was measured at various test points over the sixty-nine (69) day period. As shown in FIG. 15, the present glucose sensor provides a response over 10 nA for a period of at least sixty-nine (69) days, and/or at least two thousand two hundred fifty (2,250) samples.

EXAMPLE VIII

Figure 18B:
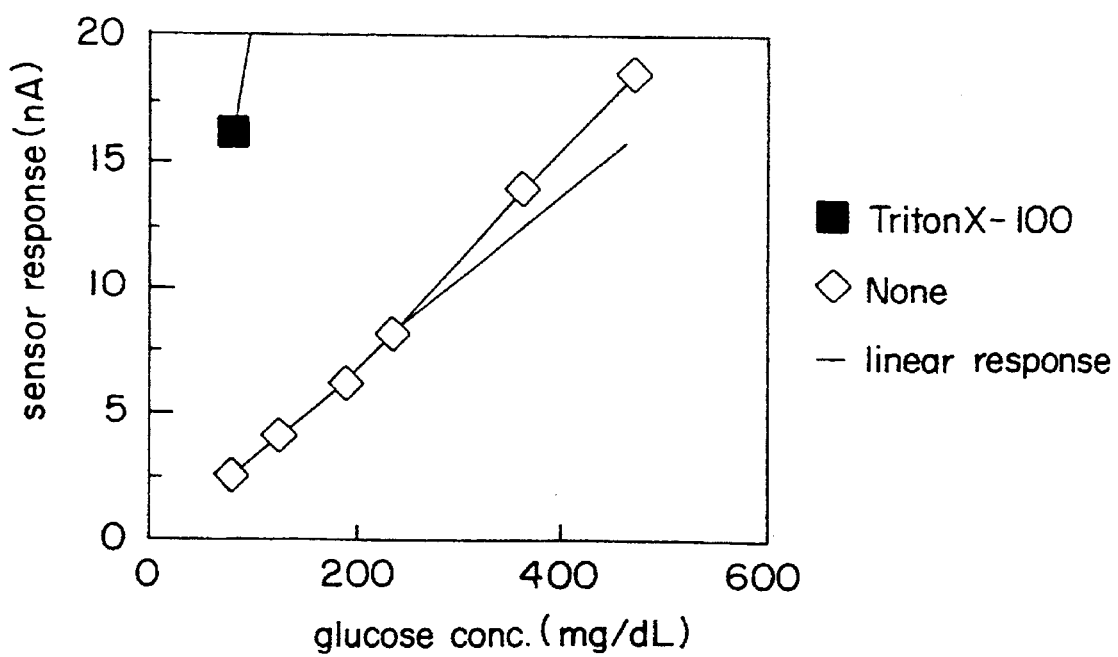
FIG. 18 is a graphical illustration of glucose sensors response to glucose concentration, after one week in storage at room temperature, with and without a surfactant post-treatment.

To determine the effect of sensor post-treatment with surfactant on the initial performance after a storage period, sensors were tested and the relationship between glucose concentration from about 83.0 mg/dl to about 470.0 mg/dl and sensor current in nanoamperes (nA) was recorded in FIG. 18. A first sensor was post-treated with Triton® X-100 (as noted above) while a second sensor was not post-treated. The sensors were stored one week at room temperature prior to the present evaluation. The untreated sensor exhibits a low and non-linear response to the glucose concentration (as shown more clearly in the exploded portion of the graphical illustration shown in FIG. 18, the response of the untreated sensor exhibits sensor drift past about 200.0 mg/dl glucose). This is the result of slow wetup caused by the membrane drying out during storage. On the other hand, the treated sensor exhibits a linear, fully wetup response after only one hour of wetup.

A variety of surfactants were evaluated to determine the effect of sensor post-treatment with a surfactant on the initial performance of the sensor. An aqueous sample having a glucose concentration of about 180.0 mg/dl was tested with five glucose sensors. The first sensor had no post-treatment, and the remaining sensors were separately post-treated with Triton® X-100 surfactant, Tergitol® 15 surfactant from Union Carbide Chemicals and Plastics Co., Inc., Danbury, Conn., Tween® 20 ethoxylated sorbitan esters surfactant and polyethylene glycol having a molecular weight of about 300. The sensors were tested and the relationship between the post-treatment and the sensor current in nanoamperes (nA) was plotted in FIG. 17. In the absence of any post-treatment, glucose sensors become difficult to wetup, as evidenced from the low response observed with untreated sensors. This effect is the result of the membrane drying out during storage. Treatment of the sensor with an antidrying agent, such as the surfactants utilized herein, more than doubled the sensor current output.

EXAMPLE IX

Figure 19:
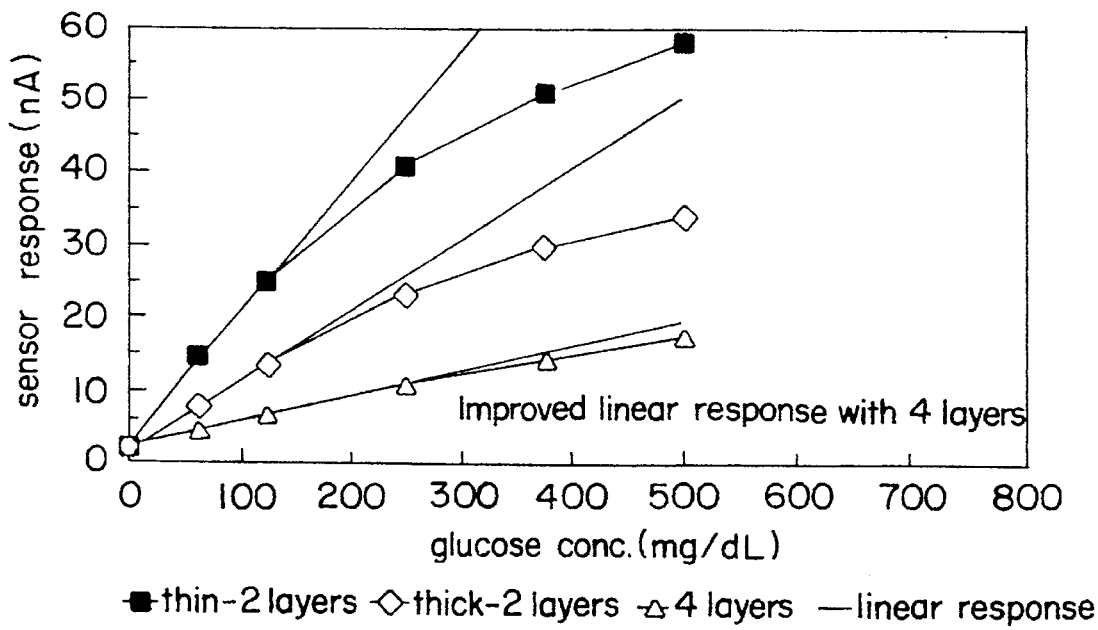
FIG. 19 is a graphical illustration of glucose sensors response to glucose concentration, and the effect of membrane thickness on the linearity of the response.

To determine the effect of membrane thickness on the linearity of a sensor's response, a thin membrane 2-layer (about 10.0 microns), a thick membrane 2-layer (about 22.0 microns), and a 4-layer membrane (about 22.0 microns) were separately evaluated. The sensors were tested and the relationship between the glucose concentration in an aqueous solution in mg/dl and sensor current in nanoamperes (nA) was plotted in FIG. 19. The multi-layer membranes were all prepared from anionically stabilized, water-based hydroxyl endblocked polydimethylsiloxane elastomer containing about 14.0 percent by weight colloidal silica, commercially available as FC-61 coating from Dow Corning, Midland, Mich. As can be observed from FIG. 19, multiple layers improve sensor performance as evidenced by a linear response. The thick 2-layer membranes of the same thickness (about 22.0 microns) as the 4-layer membranes exhibit higher output and a non-linear response to glucose. The 4-layer membrane provides improved performance due to the elimination of membrane defects. The 2-layer membrane has membrane defects which allow an excess of glucose, with respect to oxygen, to pass through the membrane thereby accounting for the non-linearity of the response, as well as the higher output.

Figure 20:
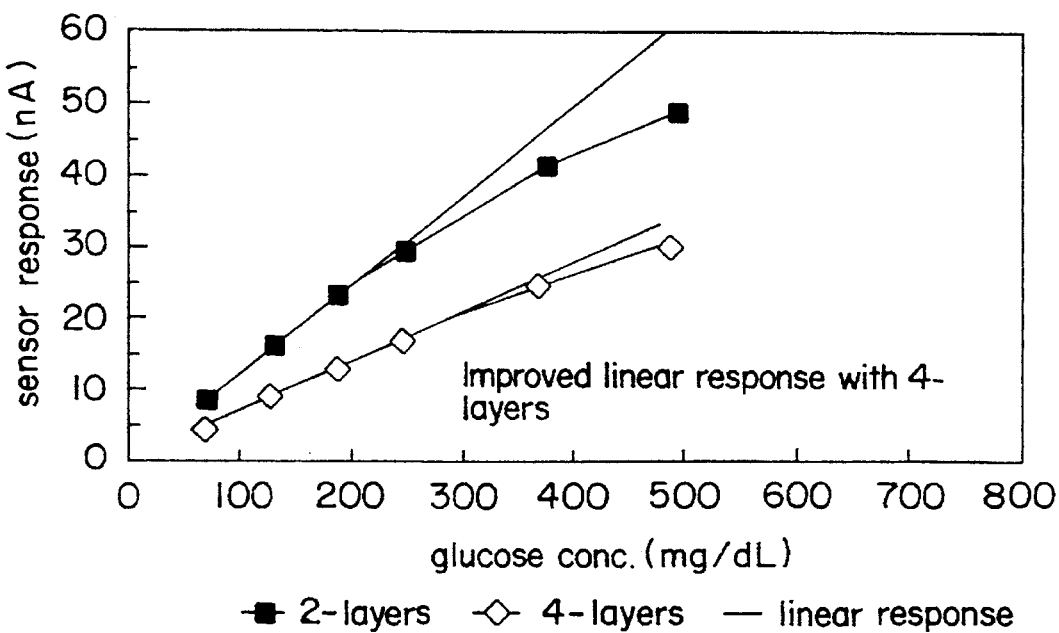
FIG. 20 is a graphical illustration of glucose sensors response to glucose concentration, and a comparison between 2-layer and 4-layer spin-cast membranes on the linearity of the response.

A similar evaluation was performed comparing a 2-layer (about 11.0 microns) and a 4-layer (about 18.0 microns) spin-cast membrane of FC-61 coating material. The sensors were tested and the relationship between the glucose concentration, ranging from about 69.0 mg/dl to about 487.0 mg/dl, and sensor current in nanoamperes (nA) was plotted in FIG. 20. Again, the 2-layer spin-cast membrane comprised defects which allowed an excess of glucose with respect to oxygen to permeate the membrane, which resulted in higher output and a non-linear response.

Figure 21A:
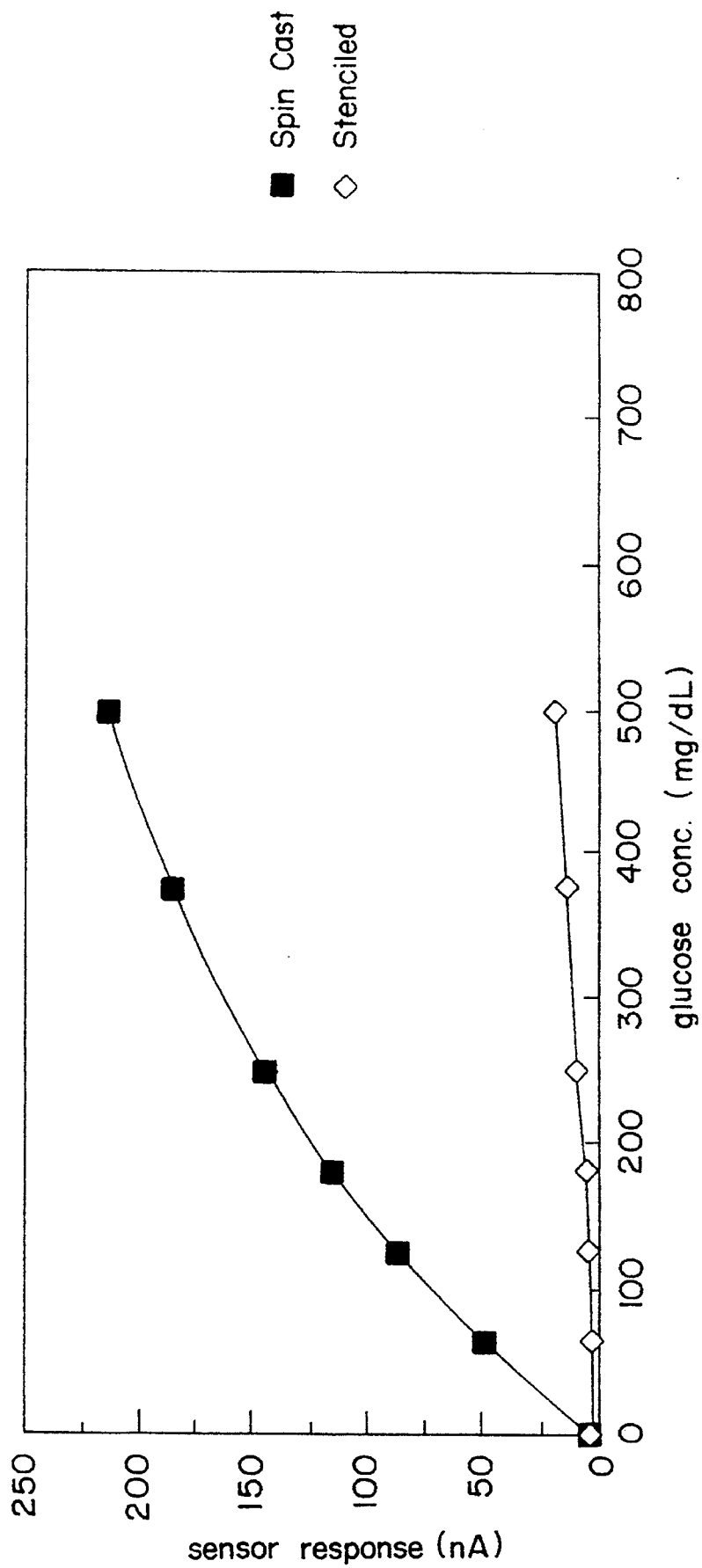
FIG. 21 is a graphical illustration of glucose sensors response to glucose concentration, and a comparison between 2-layer spin-cast and stenciled membranes on the linearity of the response.
Figure 21B:
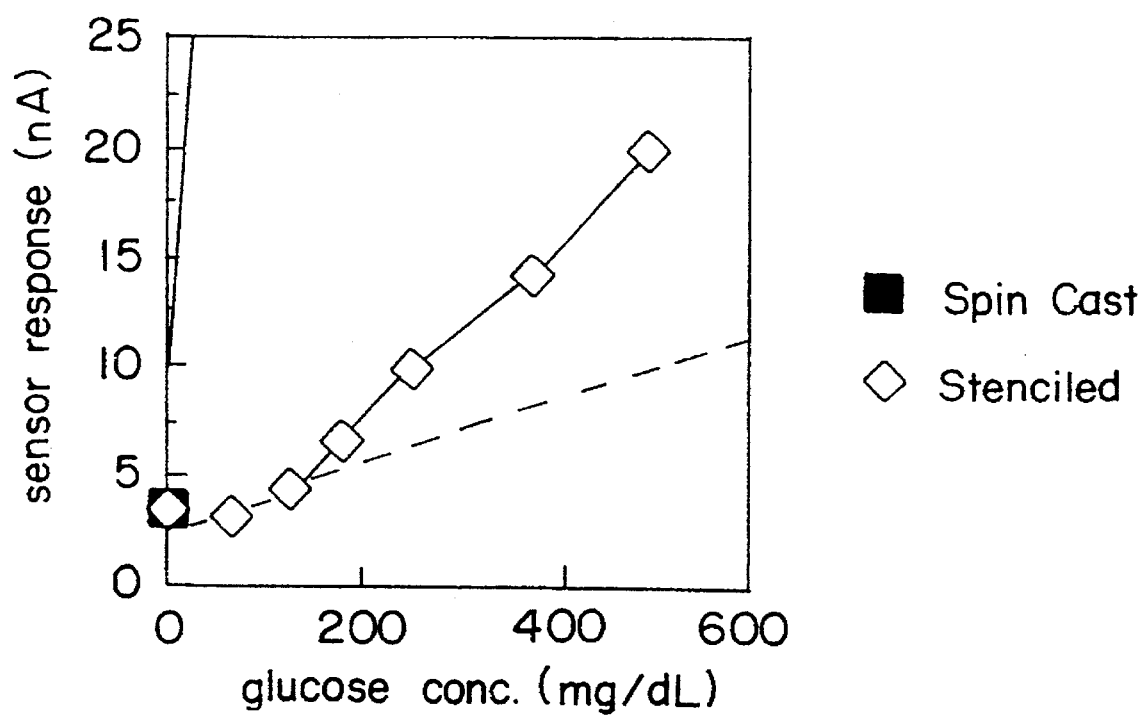

A 2-layer (about 10.0 microns) spin-cast membrane was also compared to a stenciled membrane (about 65.0 microns) to determine an effective membrane thickness. The membranes were comprised of the commercially available FC-61 coating material (as noted above). The sensors were tested and the relationship between the glucose concentration, up to about 500.0 mg/dl, and the sensor current in nanoamperes (nA) was plotted in FIG. 21. The thick, stenciled membranes exhibit slow wetup as evidenced by the non-linear glucose concentration response and the low output. It was observed that membranes with a thickness of 65.0 microns are too thick to provide for a useful glucose response. Note the positive deviation from a linear response of the stenciled film in the inset graph. Moreover, the thick stenciled membranes had a slow response time of greater than about 60 seconds. The 2-layer, spin-cast membrane exhibits high output and non-linear response (as described above).

EXAMPLE X

Figure 16:
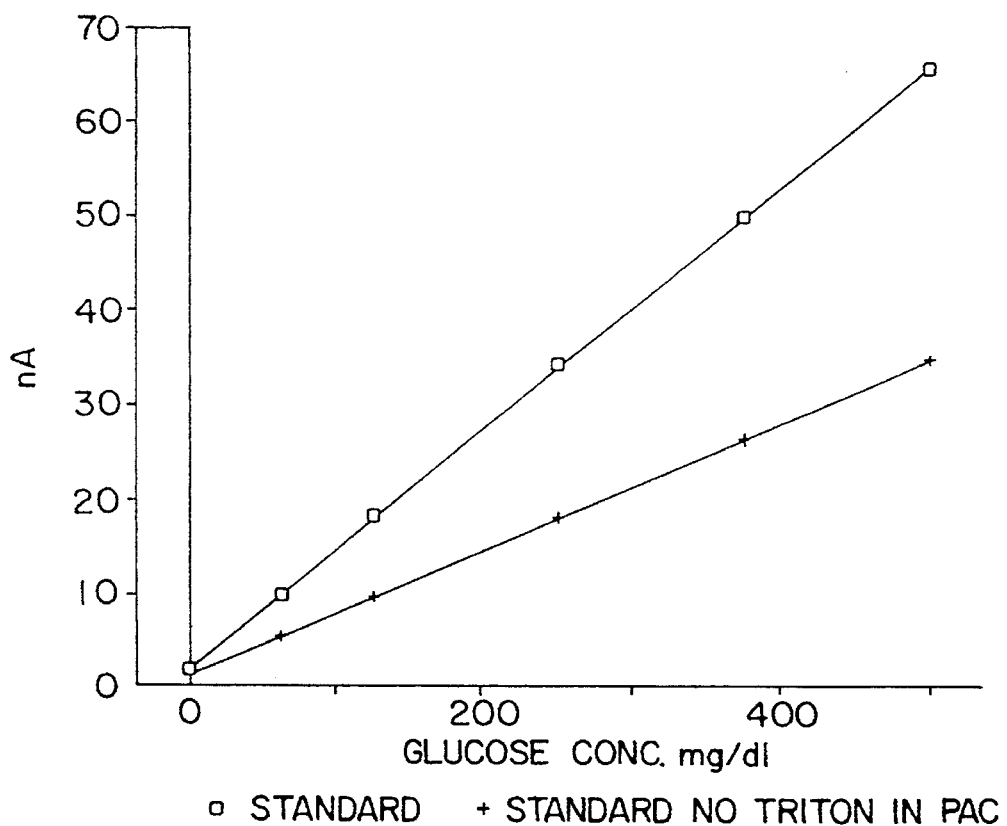
FIG. 16 is a graphical illustration of glucose sensors response to glucose concentration, with and without a surfactant post-treatment.
Figure 22:
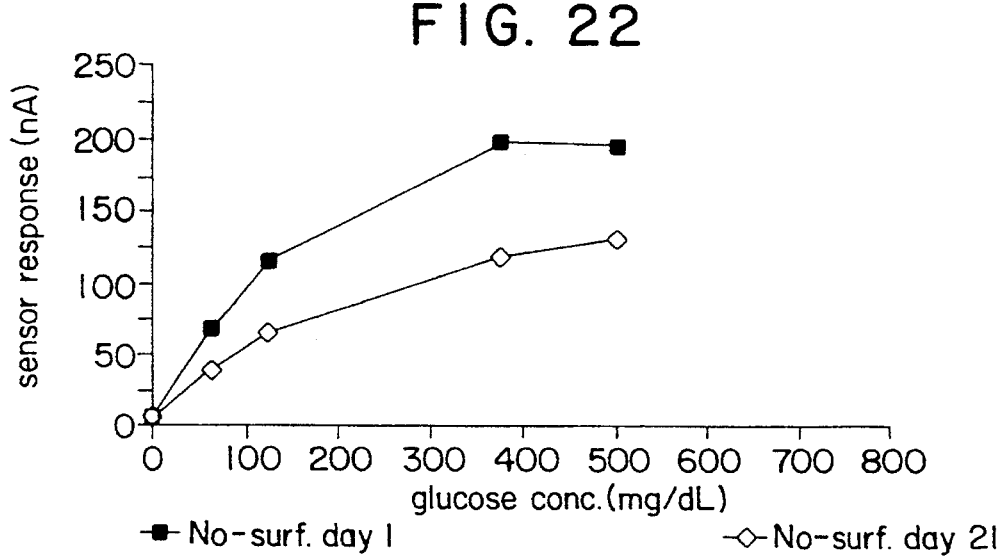
FIG. 22 is a graphical illustration of glucose sensors response to glucose concentration, and the effect of storage over an extended period of time on the response when no surfactant is added to the platinized activated carbon of the active and inactive layers of the sensor electrodes.

To determine the effect of incorporating a surfactant in the platinized activated carbon (PAC) material on performance versus storage, a glucose sensor response was evaluated with no surfactant in the PAC after one day and after 21 days in storage at room temperature. The sensors were tested and the relationship between glucose concentration, up to about 500.0 mg/dl, and sensor current in nanoamperes (nA) was plotted in FIG. 22. As shown in FIG. 22, the sensor output degrades over time if a surfactant, such as Triton® X-100, is not added to the PAC material. FIG. 16 shows the same effect as FIG. 22 but with the optimized multi-layer membrane.

Figure 23:
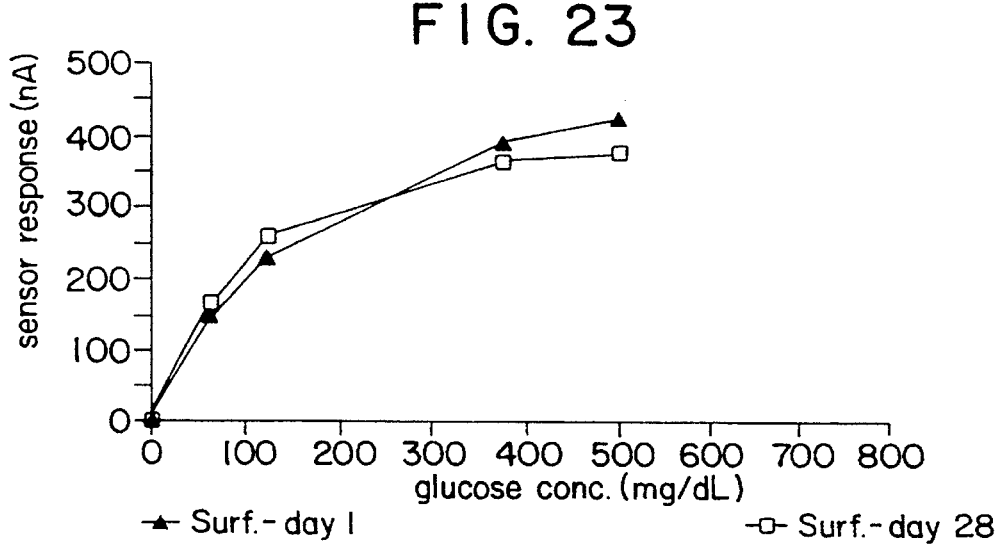
FIG. 23 is a graphical illustration of glucose sensors response to glucose concentration, and the effect of storage over an extended period of time on the response when surfactant is added to the platinized activated carbon of the active and inactive layers of the sensor electrodes.

FIG. 23 is a graphical illustration of the glucose concentration, up to about 500.0 mg/dl, and sensor current in nanoamperes (nA) wherein the glucose sensors include Triton® X-100 surfactant in the PAC material. The addition of the surfactant to the PAC, active and inactive layers, aids in sensor wetup of aged sensors. The addition of the surfactant in the PAC material provides for equivalent performance in new and aged sensors.

EXAMPLE XI

Figure 17:
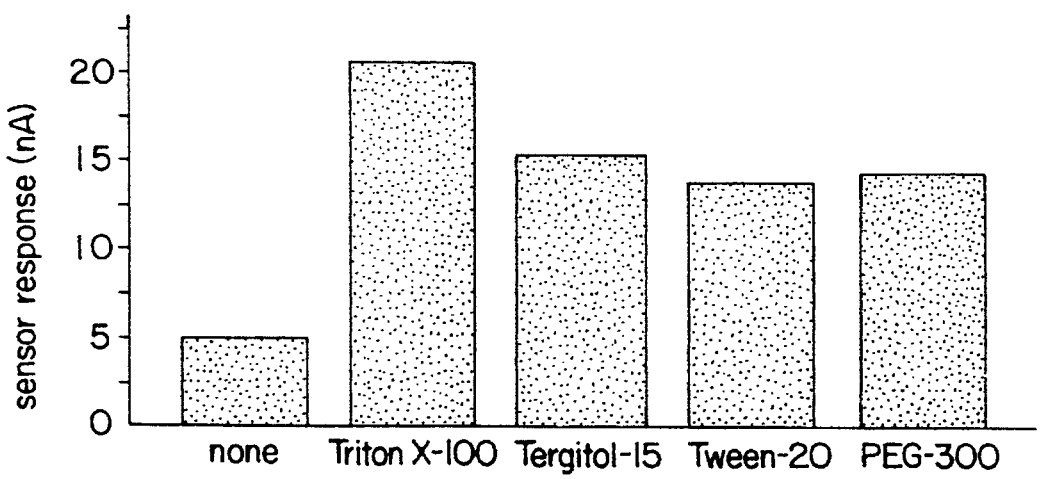
FIG. 17 is a graphical illustration of glucose sensors response to glucose concentration, with a variety of surfactant post-treatments.
Figure 24:
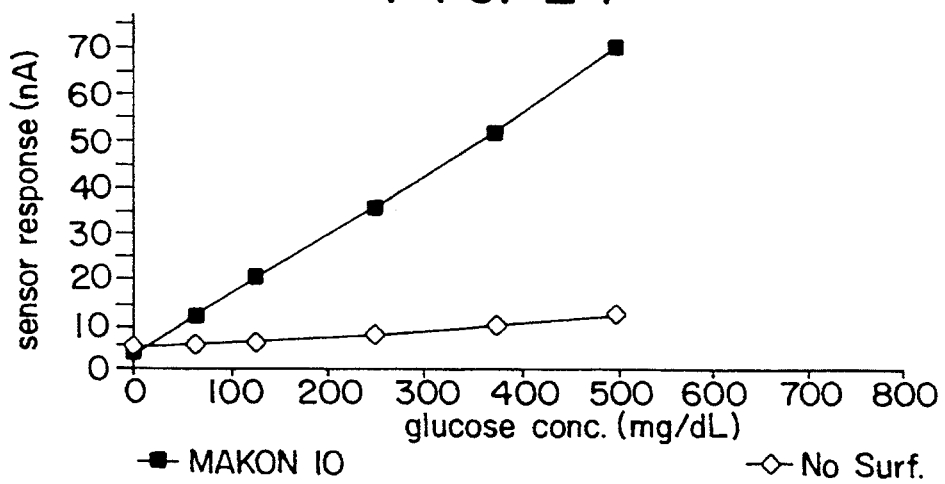
FIG. 24 is a graphical illustration of glucose sensors response to glucose concentration, and the effect of adding a surfactant material to the membrane material covering the sensor electrodes.

To determine the effect of adding a surfactant to membrane 94 on the sensors performance, glucose sensors were tested and the relationship between glucose concentration, up to about 500.0 mg/dl, and sensor current in nanoamperes (nA) was plotted in FIG. 24. The sensor membrane 94, comprised essentially of the commercially available FC-61 coating material (as described above) was applied to separate sensors; one sensor also included a surfactant material, Makon® 10 surfactant available from Stepan Co., Northfield, Ill. Both membranes were 2-layer, spin-cast membranes about 11.0 microns thick. The addition of a surfactant in the membrane provides improved wetup and higher response to glucose concentration. This effect can be minimized, although not eliminated if membranes are post-treated with an antidrying agent, as shown in FIGS. 17 and 18.

Although particular embodiments of the invention have been described in detail for purposes of illustration, various modifications may be made without departing from the spirit and scope of the present invention. Design considerations may alter the configuration of the sensor and/or the sensor package to optimize the efficiency of certain applications and minimize the cost associated with the production and use thereof. Accordingly, this invention is not to be limited except by the appended claims.

TABLE I

| | SCREEN PRINTED LAYERS | | |
|---|---|---|---|
| LAYER | INK | OVEN/ FURNACE | TEMP./ RECIPE |
| 1 | GOLD | FURNACE | STD-850 |
| 2 | PLATINUM | FURNACE | PTDI-750 |
| 3 | SILVER | FURNACE | PTDI-750 |
| 4 | DIELECTRIC | FURNACE | PTDI-750 |

TABLE I-continued

| | SCREEN PRINTED LAYERS | | |
|---|---|---|---|
| LAYER | INK | OVEN/ FURNACE | TEMP./ RECIPE |
| 5 | Ag/AgCl | OVEN | 75° C. 30 MINUTES |
| 6 | CELLULOSE ACETATE | OVEN | 55° C. 10 MINUTES RAMP TO 100° C. 10 MINUTES 100° C. 10 MINUTES |
| 7 | BSA-PAC (INACTIVE) | OVEN | 55° C. 20 MINUTES |
| 8 | GLUCOSE OXIDASE (ACTIVE) | OVEN | 55° C. 20 MINUTES |

What is claimed is:

1. A sensor package, comprising:
   a housing having a recess formed therein, said recess having a perimeter and at least one passageway connected to said recess;
   a solid state, planar electrochemical sensor underlying said recess,
   a gasket contacting said recess perimeter and said solid state, planar electrochemical sensor to form a seal therebetween; and
   a contact lead assembly, comprising:
      a contact lead frame having a first end and a second end; and
      a plurality of leads having a first end secured to said first end of said frame and a second end adjacent to said second end of said frame, and
      a stabilizer ban extending between and contacting said plurality of leads, said housing, gasket and sensor defining a sample chamber.

2. The sensor package of claim 1, wherein said contact lead frame further comprises a stabilizer bar secured to said plurality of leads to maintain each lead in predetermined position and aligning said leads with contact pads on a surface of said electrochemical sensor.

3. The sensor package of claim 2, wherein said sample chamber has a volume of from about 3.0 to about 5.0 microliters.

4. The sensor package of claim 1, wherein said contact lead frame assembly further comprises a recess in said housing for receipt of said stabilizer bar when said plurality of leads are properly positioned within said package.

5. The sensor package of claim 4, wherein said second end of said plurality of leads is disposed within said recess of said contact lead frame.

6. The sensor package of claim 5, wherein said recess of said contact lead frame is adjacent said second end of said contact lead frame.

7. The sensor package of claim 1, wherein said package further comprises a sensor pad for supporting said sensor in said recess.

8. The sensor package according to claim 7, wherein said sensor pad is disposed between said housing and said contact lead assembly.

9. The sensor package according to claim 8, further comprising said sensor disposed along said sensor pad.

10. The sensor package according to claim 7, wherein said sensor is disposed between said sensor pad and said housing.

11. The sensor package according to claim 10, wherein second end of said plurality of leads is disposed adjacent said sensor.

12. The sensor package according to claim 11, wherein said second end of said plurality of leads is disposed between said sensor and said housing.

13. The sensor package according to claim 7, further comprising a sensor disposed along said sensor pad and said sensor pad is a rubber.

14. The sensor package according to claim 13, wherein said sensor is disposed between said sensor pad and said housing.

15. The sensor package of claim 1, wherein said sample chamber further comprises a velocity compensator.

16. The sensor package of claim 15, wherein said velocity compensator is a molded part of said housing facing said sensor.

17. The sensor package of claim 1, wherein at least one of said plurality of leads provides a contact area for connection of said leads to an electrical testing system.

18. An electrochemical sensor package, comprising:
 a housing having a recess including an inlet and an outlet forming a flow path through said housing, said inlet having a first cross-section in a direction perpendicular to said flow path, said outlet having a second cross-section in a direction perpendicular to said flow path, said first cross-section being substantially equal to said second cross-section;
 a solid state planar electrochemical sensor;
 a gasket contacting said recess and said electrochemical sensor to form a sealed chamber; and
 a velocity compensator comprising a fixed in place structural barrier mounted in said flow path between said inlet and said outlet, a cross-section of said flow path in a direction perpendicular to said flow path at said velocity compensator being substantially equal to said first cross-section.

19. The sensor package of claim 18, wherein said chamber is a molded plastic chamber and said velocity compensator is an integral extension thereof.

20. The sensor package of claim 18, wherein said chamber has a volume of from about 3.0 to microliters about 5.0 microliters,
 said sensor package further comprising a plurality of contact leads, a contact lead assembly having a contact lead frame and a stabilizer bar extending between and contacting said plurality of contact leads.

* * * * *